(12) United States Patent
Hovland et al.

(10) Patent No.: US 8,735,436 B2
(45) Date of Patent: May 27, 2014

(54) POLYUNSATURATED FATTY ACIDS FOR THE TREATMENT OF DISEASES RELATED TO CARDIOVASCULAR, METABOLIC AND INFLAMMATORY DISEASE AREAS

(75) Inventors: Ragnar Hovland, Nesoddtangen (NO); Anne Kristin Holmeide, Oslo (NO); Tore Skjæret, Oslo (NO); Morten Brændvang, Sandefjord (NO)

(73) Assignee: Pronova Biopharma Norge AS, Baerum (NO)

( * ) Notice: Subject to any disclaimer, the term of this patent is extended or adjusted under 35 U.S.C. 154(b) by 23 days.

(21) Appl. No.: 13/319,101
(22) PCT Filed: May 7, 2010
(86) PCT No.: PCT/IB2010/001251
§ 371 (c)(1),
(2), (4) Date: Jan. 24, 2012
(87) PCT Pub. No.: WO2010/128401
PCT Pub. Date: Nov. 11, 2010

(65) Prior Publication Data
US 2012/0122940 A1    May 17, 2012

Related U.S. Application Data
(60) Provisional application No. 61/176,503, filed on May 8, 2009.

(51) Int. Cl.
C07D 263/20    (2006.01)
A61K 31/23     (2006.01)
A61K 31/19     (2006.01)
A61K 31/20     (2006.01)
C07C 69/732    (2006.01)
C07C 67/08     (2006.01)
C07C 59/01     (2006.01)

(52) U.S. Cl.
USPC ........... 514/376; 514/549; 514/557; 514/558; 514/560; 560/183; 560/205; 562/579

(58) Field of Classification Search
USPC .......... 514/376, 549, 557, 558, 560; 560/183, 560/205; 562/579
See application file for complete search history.

(56) References Cited

U.S. PATENT DOCUMENTS 2,909,554 A    10/1959  Doerr
4,009,211 A    2/1977   Onopchenko et al.
(Continued)

FOREIGN PATENT DOCUMENTS

CA    2115345       2/1993
CN    1248916 A     3/2000
(Continued)

OTHER PUBLICATIONS

Larsen, L.N. et al, "Sulfur-Substituted and α-Methylated FAtty ACids as Peroxisome Proleferator-Activated Receptor Activators," *Lipids*, 40:49-57, 2005.

(Continued)

*Primary Examiner* — Ernst Arnold
*Assistant Examiner* — Kyung Sook Chang
(74) *Attorney, Agent, or Firm* — Finnegan, Henderson, Farabow, Garrett & Dunner LLP

(57) ABSTRACT

The present disclosure relates to lipid compounds of the general formula (I):

$$R_1\text{-O---C}(R_2)(R_3)\text{-X} \qquad (I)$$

wherein $R_1$ is a $C_{10}$-$C_{22}$ alkyl group, a $C_{10}$-$C_{22}$ alkenyl group having 1-6 double bonds, or a $C_{10}$-$C_{22}$ alkynyl group having 1-6 triple bonds; $R_2$ and $R_3$ are the same or different and may be chosen from different substituents; and X is a carboxylic acid or a derivative thereof, such as a carboxylic ester, a carboxylic anhydride, a phospholipid, triglyceride, or a carboxamide; or a pharmaceutically acceptable salt, solvate, solvate of such salt or a prodrug thereof. The present disclosure also relates to pharmaceutical compositions and lipid compositions comprising at least one compound according to the present disclosure, and to such compounds for use as medicaments or for use in therapy, in particular for the treatment of diseases related to the cardiovascular, metabolic, and inflammatory disease area.

46 Claims, 2 Drawing Sheets

(56) References Cited

U.S. PATENT DOCUMENTS

| | | | |
|---|---|---|---|
| 4,032,564 | A | 6/1977 | Henrick et al. |
| 4,040,781 | A | 8/1977 | Lamberti et al. |
| 4,209,410 | A | 6/1980 | Baldwin |
| 4,214,088 | A | 7/1980 | Abeler et al. |
| 4,286,053 | A | 8/1981 | Ishikawa et al. |
| 4,297,268 | A | 10/1981 | Abeler et al. |
| 4,368,190 | A | 1/1983 | Shen et al. |
| 4,411,808 | A | 10/1983 | Gutierrez et al. |
| 4,444,766 | A | 4/1984 | Bosies et al. |
| 5,306,754 | A | 4/1994 | Yamamoto et al. |
| 5,328,953 | A | 7/1994 | Lynch |
| 5,447,820 | A | 9/1995 | Hayakawa et al. |
| 5,612,093 | A | 3/1997 | Braig et al. |
| 5,763,517 | A | 6/1998 | Yamamoto et al. |
| 5,770,584 | A | 6/1998 | Kucera et al. |
| 5,990,173 | A | 11/1999 | Patoiseau et al. |
| 6,060,515 | A | 5/2000 | Elias et al. |
| 6,365,628 | B1 | 4/2002 | Berge |
| 6,376,688 | B1 | 4/2002 | Ferrante et al. |
| 6,511,670 | B1 | 1/2003 | Maignan et al. |
| 6,624,190 | B2 | 9/2003 | Khoury et al. |
| 6,723,717 | B1 | 4/2004 | Youngquist et al. |
| 7,250,456 | B2 | 7/2007 | Eigen et al. |
| 7,273,852 | B2 | 9/2007 | Tsuji et al. |
| 7,427,583 | B2 | 9/2008 | Couillet et al. |
| 7,517,858 | B1 | 4/2009 | Hostetler et al. |
| 7,902,399 | B2 | 3/2011 | Berge et al. |
| 7,968,617 | B2 | 6/2011 | Thalacker et al. |
| 8,304,551 | B2 | 11/2012 | Milne et al. |
| 2003/0147814 | A1 | 8/2003 | Scherrer et al. |
| 2004/0126424 | A1 | 7/2004 | Jandacek et al. |
| 2005/0107503 | A1 | 5/2005 | Couillet et al. |
| 2006/0135785 | A1 | 6/2006 | Patoiseau et al. |
| 2006/0247458 | A1 | 11/2006 | Yamamoto et al. |
| 2007/0060497 | A1 | 3/2007 | Krahmer et al. |
| 2007/0167529 | A1 | 7/2007 | Walton et al. |
| 2007/0254862 | A1 | 11/2007 | Antel et al. |
| 2009/0137567 | A1 | 5/2009 | Perrine et al. |
| 2010/0280109 | A1 | 11/2010 | Holmeide |
| 2011/0190395 | A1 | 8/2011 | Holmeide et al. |
| 2012/0122940 | A1 | 5/2012 | Hovland et al. |
| 2012/0252850 | A1 | 10/2012 | Milne et al. |
| 2012/0264791 | A1 | 10/2012 | Milne et al. |
| 2013/0046013 | A1 | 2/2013 | Hovland et al. |

FOREIGN PATENT DOCUMENTS

| | | | |
|---|---|---|---|
| CN | 101225064 | | 7/2008 |
| EP | 0 002 007 | | 5/1979 |
| EP | 0 050 327 | | 4/1982 |
| EP | 0 175 591 | A2 | 3/1986 |
| EP | 0 399 183 | | 11/1990 |
| EP | 0 463 947 | | 1/1992 |
| GB | 1038723 | | 8/1966 |
| GB | 1523276 | | 8/1978 |
| JP | 04-051149 | | 2/1992 |
| JP | 11-180929 | | 7/1999 |
| WO | WO 97/38688 | A1 | 10/1997 |
| WO | WO 00/72920 | | 12/2000 |
| WO | WO 01/98328 | | 12/2001 |
| WO | WO 03/014073 | | 2/2003 |
| WO | WO 2005/073164 | A1 | 8/2005 |
| WO | WO 2006/025246 | | 3/2006 |
| WO | WO 20061094915 | A2 | 9/2006 |
| WO | WO 2006/117664 | | 11/2006 |
| WO | WO 2006/117668 | | 11/2006 |
| WO | WO 2007/116027 | | 10/2007 |
| WO | WO 2008/053331 | A1 | 5/2008 |
| WO | WO 2008/053340 | A1 | 5/2008 |
| WO | WO 2008125241 | A1 * | 10/2008 ............ 526/96 |
| WO | WO 2009/061208 | | 5/2009 |
| WO | WO 2009/149496 | | 12/2009 |
| WO | WO 2009/156621 | | 12/2009 |
| WO | WO 2010/006085 | | 1/2010 |
| WO | WO 2010/008299 | | 1/2010 |
| WO | WO 2010/128401 | | 11/2010 |
| WO | WO 2011/089529 | A1 | 7/2011 |
| WO | WO 2012/059818 | | 5/2012 |
| WO | WO 2012/115695 | | 8/2012 |
| WO | WO 2013/016531 | | 1/2013 |

OTHER PUBLICATIONS

International Search Report for PCT/IB2010/001251 dated Oct. 4, 2010.
Berge, S.M. et al., "Pharmaceutical Salts," *J. Pharmaceutical Sciences* (1977) 66(1):1-19.
English counterpart International Patent Application Publication WO 98/032444 of CN 1248916A, (1998).
English machine translation of JP 11-180929, (1999).
Nystrom, R.F. & Brown, W.G., "Reduction of Organic Compounds by Lithium Aluminum Hydride. II. Carboxylic Acids," *Journal of the American Chemical Society* (1947) 69(10):2548-2549.
Office Action dated Aug. 3, 2012, from U.S. Appl. No. 12/741,890.
Office Action dated Aug. 6, 2013, from U.S. Appl. No. 12/741,890.
Office Action dated Dec. 10, 2012, from U.S. Appl. No. 12/741,890.
Shchepin, R. et al., "Quorum Sensing in *Candida albicans*: Probing Farnesol's Mode of Action with 40 Natural and Synthetic Farnesol Analogs," (2003) *Chemistry & Biology* 10:743-750.
Stahl, P.H. & Wermuth, C.G., "Chapter 12: Monographs on Acids and Bases," at 265-327, in "Handbook of Pharmaceutical Salts: Properties, Selection, and Use.", (2008).
Togashi, N. et al., "Antibacterial Activity of Long-Chain Fatty Alcohols Against *Staphylococcus aureus*," *Molecules* (2007) 12:139-148.
Tsotinis, A., "Synthesis and Antiretroviral Evaluation of New Alkoxy and Aryloxy Phosphate Derivatives of 3'-Azido-3'-deoxythymidine," *J. Med. Chem.* (1996) 39:3418-3422.
Ahmad, J. et al., "Reactions in Monolayers: Base-Catalyzed Ester Hydrolysis Revisited," *Langmuir* (1990) 6:1797-1799.
Copending U.S. Appl. No. 12/741,890, filed Jul. 27, 2010.
Copending U.S. Appl. No. 13/054,212, filed Apr. 13, 2011.
Copending U.S. Appl. No. 13/574,132, filed Jul. 19, 2012.
Copending U.S. Appl. No. 13/883,405, filed May 3, 2013.
Derzhinskii, A.R. et al., "Functional Sulfur-Containing Compounds. Part 4. Preparation of Chloro(Bromo)Alkyl Sulfones by Oxidative Halogenation of Hydroxyalkyl Sulfides and Sulfoxides with Mixtures of Hydrogen Peroxide and a Hydrohalic Acid," *Izvestiya Akademii Nauk SSSR Seriya Khimicheskaya* (1982) 31(5):995-1001.
English abstract of CN 101225064, (2008).
English abstract of EP 0 463 947, (1995).
English abstract of JP 04-051149, (1992).
Ferrell, W.J., "Synthesis and Properties of $^{35}S$, $^{14}C$ and $^3H$ Labeled S-Alkyl Glycerol Ethers and Derivatives," *Chemistry and Physics of Lipids* (1976) 16:276-284.
Ferrucci, L. et al., "Relationship of Plasma Polyunsaturated Fatty Acids to Circulating Inflammatory Markers," *J. Clin. Endocrin. & Metab.* (2006) 91(2):439-446.
Flock et al., "Syntheses of Some Polyunsaturated Sulfur- and Oxygen-Containing Fatty Acids Related to Eicosapentaenoic and Docosahexaenoic Acids," *Acta Chemica Scandinavica* (1999) 53:436-445.
Geleijnse, J.M. et al., "Blood Pressure Response to Fish Oil Supplementation: Metaregression Analysis of Randomized Trials," *J. Hypertension* (2002) 20(8):1493-1499.
Goldsworthy et al., "Some Sulphides Containing the 2-Chloroethyl Group," *Journal of the Chemical Society* (1948) 2177-2179.
Grupp, I.L. et al., "Protection Against Hypoxia-Reoxygenation in the Absence of Poly (ADP-Ribose) Synthetase in Isolated Working Hearts," *J. Mol. Cell Cardiol.* (1999) 31:297-303.
Hermetter, A. & Paltauf, F., "A Facile Procedure for the Synthesis of Saturated Phosphatidylcholines," *Chemistry & Physics of Lipids* (1981) 28:111-115.
Hill, A.J. & Fager, E.W., "Some α-Alkylthio Aliphatic Acids," *Journal of the American Chemical Society* (1943) 65(12):2300-2301.

(56) References Cited

OTHER PUBLICATIONS

Holmeide, A.K. & Skattenbol, L., "Syntheses of Some Polyunsaturated Trifluoromethyl Ketones as Potential Phospholipase $A_2$ Inhibitors," *J. Chem. Soc., Perkin Trans.* (2000) 1:2271-2276.

Hosokawa, M. et al., "Preparation of Therapeutic Phospholipids Through Porcine Pancreatic Phospholipase $A_2$-Mediated Esterification and Lipozyme-Mediated Acidolysis," *J. Am. Oil Chem. Soc.* (1995) 72(11):1287-1291.

International Search Report for International Application No. PCT/IB2011/000250 dated May 31, 2011.

International Search Report for International Application No. PCT/IB2011/002925 dated Mar. 5, 2012.

International Search Report for International Application No. PCT/NO2008/000391 dated Feb. 4, 2009.

International Search Report for International Application No. PCT/NO2009/000262 dated Oct. 23, 2009.

Jones, P.B. et al., "A New Class of Antituberculosis Agents," *J. Med. Chem.* (2000) 43:3304-3314.

Kasai, Y. et al., "Synthesis of Diphenylalkane Sulfonate and Its Surface Activity," *Kogyo Kagaku Zasshi* (1965) 68(11):2073-2077.

Lamango, N.S. et al., "Inhibition Mechanism of S-Adenosylmethionine-Induced Movement Deficits by Prenylcysteine Analogs," *Pharmacology, Biochemistry, & Behavior* (2003) 76:433-442.

Larsen, L.N. et al, "α- and β-Alkyl-Substituted Eicosapentaenoic Acids: Incorporation into Phospholipids and Effects on Prostaglandin H Synthase and 5-Lipoxygenase," *Biochemical Pharmacology* (1998) 55:405-411.

Lilja-Hallberg, M. & Harrod, M., "Enzymatic Esterification of Long Polyunsaturated Fatty Acids and Lyso-Phosphatidylcholine in Isooctane and Ethanol," *Biocatalysis* (1994) 9:195-207.

Livingston, J.R. & Drogin, R., "The Synthesis and Some Surface Active Properties of Alkylthioalkyl and Alkoxyalkyl Sulfates," *The Journal of the American Oil Chemists' Society* (1965) 42:720-723.

Masson, M. et al., "Marine Lipids for Prodrugs, Soft Compounds and Other Pharmaceutical Applications," *Pharmazie* (2000) 55(3):172-177.

Meyer, K.L. et al., "In Vivo Evaluation of Phosphocholine and Quaternary Ammonium Containing Lipids as Novel Anti-HIV Agents," *J. Med. Chem.* (1991) 34(4):1377-1383.

Office Action dated Apr. 1, 2013, from U.S. Appl. No. 13/054,212.
Office Action dated Jan. 31, 2013, from U.S. Appl. No. 13/319,101.
Office Action dated Jul. 1, 2013, from U.S. Appl. No. 13/054,212.

Okoronkwo, A.E. et al., "Synthesis of ω-Hydroxy-α-Alkyl/Aryl-γ-Organo-Selenium and γ-Organo-Tellurium: A New Class of Organochalcogen Compounds with Antinociceptive Activity," *Tetrahedron Letters* (2008) 49:3252-3256.

Parkkari, T. et al., "α-Methylated Derivatives of 2-Arachidonoyl Glycerol: Synthesis, CB1 Receptor Activity, and Enzymatic Stability," *Bioorg. & Med. Chem. Lett.* (2006) 16:2437-2440.

Pitt, M.J. et al., "Synthesis of Polyunsaturated β-Oxa Fatty Acids Via Rhodium Mediated Carbenoid Insertion," *Synthesis* (1997) 7:1240-42.

Registry Copyright 2008 ACS on STN (RN 785712-42-7, 714185-72-5, 45247-37-8).

Rossmeisl, M. et al., "Prevention and Reversal of Obesity and Glucose Intolerance in Mice by DHA Derivatives," *Obesity* (2009) 17(5):1023-1031.

Shirley, D.A. et al., "Alkylation with Long Chain p-Toluenesulfonates. IV. Alkylation of Alcohols and Amines with n-Octadecyl p-Toluenesulfonate," *Journal of Organic Chemistry* (1953) 18:378-381.

Silverman, R.B., The Organic Chemistry of Drug Design and Drug Action, 1992, Academic Press, pp. 4, 14-28.

Simopoulos, A.P., "Essential Fatty Acids in Health and Chronic Disease," *Am. J. Clin. Nutr.* (1999) 70(Suppl):560S-569S.

Srisiri, W. et al., "Syntheses of Polymerizable Monoacylglycerols and 1,2-Diacyl-sn-Glycerols," *J. Org. Chem.* (1996) 61(16):5911-5915.

Storlien, L.H. et al., "Polyunsaturated Fatty Acids, Membrane Function and Metabolic Diseases Such As Diabetes and Obesity," *Curr. Opin. In Clin. Nutr. & Metab. Care* (1998) 1(6):559-563.

Tran, P.O.T. et al., "Inhibition of Interleukin-1β-Induced COX-2 and EP3 Gene Expression by Sodium Salicylate Enhances Pancreatic Islet β-Cell Function," *Diabetes* (2002) 51:1772-78.

Vaagenes, H. et al., "Methylated Eicosapentaenoic Acid and Tetradecylathioacetic Acid: Effects on Fatty Acid Metabolism," *Biochem. Pharmacol.* (1999) 58:1133-1143.

Wang, P. et al., "Synthesis of Phospholipid-Inhibitor Conjugates by Enzymatic Transphosphatidylation with Phospholipase D," *J. Am. Chem. Soc.* (1993) 115:10487-10491.

Willumsen, N. et al., "Enhanced Hepatic Fatty Acid Oxidation and Upregulated Carnitine Palmitoyltransferase II Gene Expression by Methyl 3-Thiaoctadeca-6,9,12,15-Tetraenoate in Rats," *J. Lipid Mediators Cell Signalling* (1997) 17:115-134.

Willumsen, N. et al., "On the Effect of 2-Deuterium- and 2-Methyl-Eicosapentaenoic Acid Derivatives on Triglyerides, Peroxisomal β-Oxidation and Platelet Aggregation in Rats," *Biochimica et Biophysica Acta* (1998) 1369:193-203.

Woodbury, D.M. & Fingle, E., "Drugs Effective in the Therapy of the Epilepsies," *Basis of Therapeutics* 201-26 (5th Ed. 1975).

Zeinalov, B.K., "Synthesis and Investigation of Esters of Alkyl Selenium Ethanols," *Azerbajdzanskij Chimiceskij Zurnal* (1981) 5:41-43.

\* cited by examiner

POLYUNSATURATED FATTY ACIDS FOR THE TREATMENT OF DISEASES RELATED TO CARDIOVASCULAR, METABOLIC AND INFLAMMATORY DISEASE AREAS

PRIORITY

This application claims the benefit of priority of U.S. Provisional Patent Application No. 61/176,503, filed May 8, 2009, the contents of which is incorporated herein by reference.

This is a national stage application under §371 of PCT/IB2010/001251, filed on May 7, 2010, which as mentioned above, claims the benefit of priority of U.S. Provisional Patent Application No. 61/176,503, filed on May 8, 2009. These applications are incorporated herein by reference.

TECHNICAL FIELD

The present disclosure relates to lipid compounds of the general formula (I):

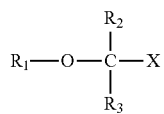
(I)

wherein
  $R_1$ is a $C_{10}$-$C_{22}$ alkyl group, a $C_{10}$-$C_{22}$ alkenyl group having 1-6 double bonds, or a $C_{10}$-$C_{22}$ alkynyl group having 1-6 triple bonds;
  $R_2$ and $R_3$ are the same or different and may be chosen from a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, with the proviso that $R_2$ and $R_3$ cannot both be a hydrogen atom; or
  $R_2$ and $R_3$ together form a cycloalkyl group, such as cyclopropane, cyclobutane, cyclopentane, or cyclohexane;
  X is a carboxylic acid or a derivative thereof, such as, a carboxylic ester, a carboxylic anhydride, carboxamide, phospholipid, monoglyceride, diglyceride, or triglyceride;
or a pharmaceutically acceptable salt, solvate, solvate of such salt or a prodrug thereof.

In embodiments where $R_2$ and $R_3$ are different, the compounds of formula (I) are capable of existing in stereoisomeric forms. It will be understood that the invention encompasses all optical isomers of the compounds of formula (I) and mixtures thereof.

The present disclosure also relates to pharmaceutical compositions and lipid compositions comprising at least one compound of formula (I). In addition, the present disclosure includes compounds of formula (I) for use as medicaments or for use in therapy, such as for the treatment of diseases related to the cardiovascular, metabolic, and inflammatory disease areas.

BACKGROUND

Dietary polyunsaturated fatty acids (PUFAs) have effects on diverse physiological processes impacting normal health and chronic diseases, such as the regulation of plasma lipid levels, cardiovascular and immune functions, insulin action, neuronal development and visual function.

Due to their limited stability in vivo and their lack of biological specificity, PUFAs have not achieved widespread use as therapeutic agents. Chemical modifications of the n-3 polyunsaturated fatty acids have been performed by several research groups in order to change or increase their effects.

For example, the hypolipidemic effects of (4Z,7Z,10Z, 13Z,16Z,19Z)-docosa-4,7,10,13,16,19-hexaenoic acid (DHA) was potentiated by introducing a substituent in the α-position of (4Z,7Z,10Z,13Z,16Z,19Z)-ethyl docosa-4,7, 10,13,16,19-hexaenoate (DHA EE). (WO 2006/117664) It is reported that obese, high fat-fed mice treated with alpha-substituted DHA derivatives prevented and reversed obesity and glucose intolerance. (Rossmeisl, M., et al., Obesity (Silver Spring) 2009 Jan. 15.)

Several research groups have prepared unsaturated fatty acids with oxygen incorporated in the β-position (Flock, S. et al., Acta Chemica Scandinavica, (1999) 53: 436 and Pitt, M J, et al., Synthesis, (1997) 1240-42).

A novel group of fatty acid derivatives combining an oxygen atom in β-position with a α-substituents represented by the general formula (I) has been developed. These novel fatty acids reduce lipid levels in a dyslipidemic mice model to a greater extent than naturally occurring polyunsaturated fatty acids.

SUMMARY

Figure 1:
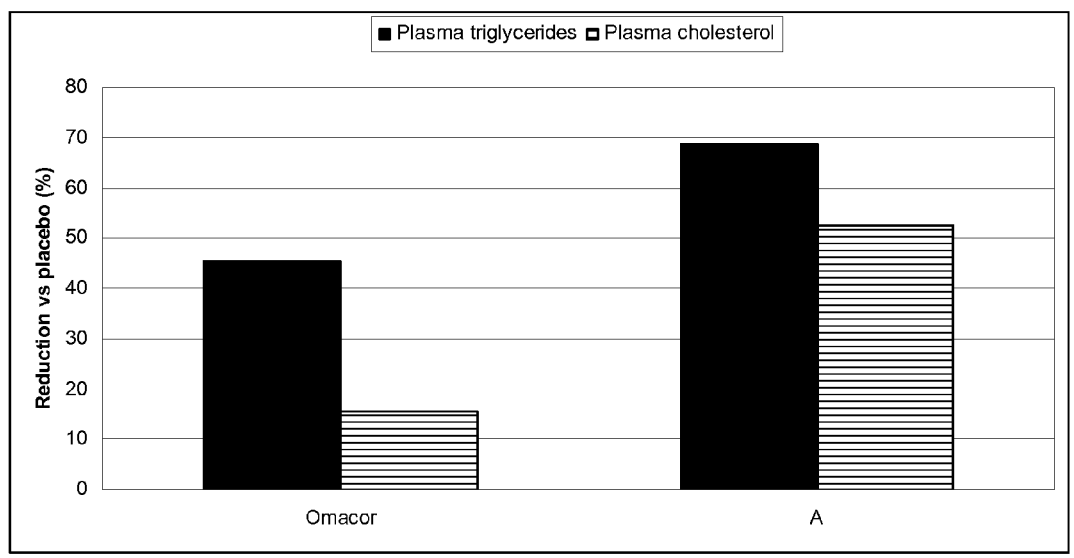
FIG. 1: Cholesterol and triglyceride levels in APOE*3Leiden mice after administration of one embodiment of the present disclosure and Omacor™.

One object of the present disclosure is to provide lipid compounds having improved biological activity compared to naturally occurring polyunsaturated fatty acids. This object may be achieved by a lipid compound of formula (I)

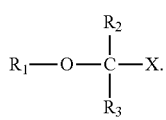
(I)

For example, the present disclosure relates to compounds of formula (I), wherein:
  $R_1$ is a $C_{10}$-$C_{22}$ alkyl group, a $C_{10}$-$C_{22}$ alkenyl group having 1-6 double bonds, or a $C_{10}$-$C_{22}$ alkynyl group having 1-6 triple bonds;
  $R_2$ and $R_3$ are the same or different and may be chosen from a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, with the provisio that $R_2$ and $R_3$ cannot both be a hydrogen atom; or $R_2$ and $R_3$ together can form a cycloalkyl group, such as cyclopropane, cyclobutane, cyclopentane, or cyclohexane;

X is a carboxylic acid or a derivative thereof, such as, a carboxylic ester, a carboxylic anhydride, a carboxamide, a phospholipid, or a triglyceride;

or a pharmaceutically acceptable salt, solvate, solvate of such salt or a prodrug thereof.

In at least one embodiment, the alkyl group may be chosen from methyl, ethyl, n-propyl, isopropyl, n-butyl, sec-butyl, and n-hexyl. The alkenyl group may be chosen from allyl, 2-butenyl, and 3-hexenyl. The alkynyl group may be chosen from propargyl, 2-butynyl, and 3-hexynyl. The halogen atom may be chosen from fluorine, chlorine, bromine, and iodine. The alkoxy group may be chosen from methoxy, ethoxy, propoxy, isopropoxy, sec-butoxy, phenoxy, benzyloxy, $OCH_2CF_3$, and $OCH_2CH_2OCH_3$. The acyloxy group may be chosen from acetoxy, propionoxy, and butyroxy. The aryl group is a phenyl group. The alkylthio group may be chosen from methylthio, ethylthio, isopropylthio, and phenylthio. The alkoxycarbonyl group may be chosen from methoxycarbonyl, ethoxycarbonyl, propoxycarbonyl, and butoxycarbonyl. The alkylsulfinyl group may be chosen from methanesulfinyl, ethanesulfinyl, and isopropanesulfinyl. The alkylsulfonyl group may be chosen from methanesulfonyl, ethanesulfonyl, and isopropanesulfonyl. The alkylamino group may be chosen from methylamino, dimethylamino, ethylamino, and diethylamino. The carboxylate group may be chosen from ethyl carboxylate, methyl carboxylate, n-propyl carboxylate, isopropyl carboxylate, n-butyl carboxylate, sec-butyl carboxylate, and n-hexyl carboxylate. The carboxamide group may be chosen from carboxamides, such as N-methyl carboxamide, N,N-dimethyl carboxamide, N-ethyl carboxamide and N,N-diethyl carboxamide.

In at least one embodiment of the invention, one of the substituents $R_2$ and $R_3$ of the compound of formula (I) is hydrogen and the other one is chosen from a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group.

In another embodiment of the invention, the substituents $R_2$ and $R_3$ of the compound of formula (I) are the same or different and may be chosen from a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group. For example, $R_2$ and $R_3$ may be chosen from methyl, ethyl, n-propyl, or isopropyl.

When derived or prepared from a polyunsaturated fatty acid, $R_1$ is typically a $C_{10}$-$C_{22}$ alkenyl group with 3-6 double bonds, e.g. 3-6 methylene interrupted double bonds in Z configuration. For example, $R_1$ may be chosen from:
a $C_{15}$ alkenyl with 4 methylene interrupted double bonds in Z-configuration,
a $C_{18}$ alkenyl with 3-5 double bonds, e.g. a $C_{18}$ alkenyl with 5 methylene interrupted double bonds in Z configuration,
a $C_{20}$ alkenyl with 5 methylene interrupted double bonds in Z-configuration, or
a $C_{22}$ alkenyl with 6 methylene interrupted double bonds in Z-configuration.

Furthermore, $R_1$ may be a $C_{10}$-$C_{22}$ alkynyl group, e.g. a $C_{16}$-$C_{22}$ alkynyl with 1-6 triple bonds.

The present disclosure also relates to salts of the compound of formula (I). Such salts may be represented by

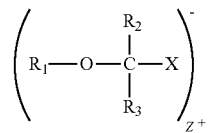

wherein X is $COO^-$, and $Z^+$ may be $NH_4^+$, a metal ion such as $Li^+$, $Na^+$, or $K^+$, a protonated primary amine such as tert-butyl ammonium, (3s,5s,7s)-adamantan-1-ammonium, 1,3-dihydroxy-2-(hydroxymethyl)propan-2-ammonium or a protonated aminopyridine (e.g., pyridine-2-ammonium), a protonated secondary amine such as diethylammonium, 2,3,4,5,6-pentahydroxy-N-methylhexan-1-ammonium, N-ethylnaphthalen-1-ammonium, a protonated tertiary amine such as 4-methylmorpholin-4-ium, a protonated guanidine such as amino((4-amino-4-carboxybutyl)amino)methaniminium or a protonated heterocycle such as 1H-imidazol-3-ium, or by

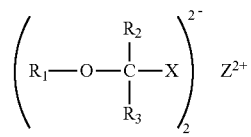

wherein $X=COO^-$, and $Z^{2+}$ may be $Mg^{2+}$ or $Ca^{2+}$, or a diprotonated diamine such as ethane-1,2-diammonium or piperazine-1,4-diium.

Another representative salt is

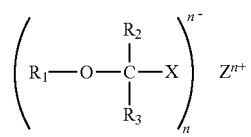

wherein X is $COO^-$, and $Z^{n+}$ is protonated Chitosan:

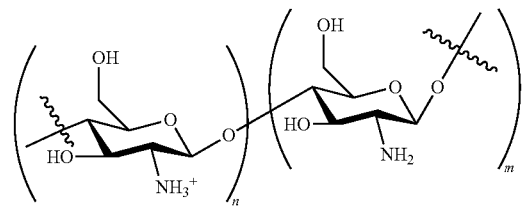

Furthermore, the present disclosure relates to compounds of formula (I), wherein X is a carboxylic acid in the form of a phospholipid. Such compounds may be represented by the following formulas (II-IV),

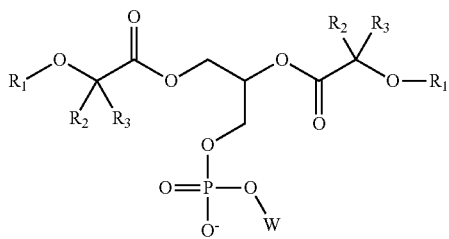
(II)
wherein W is:
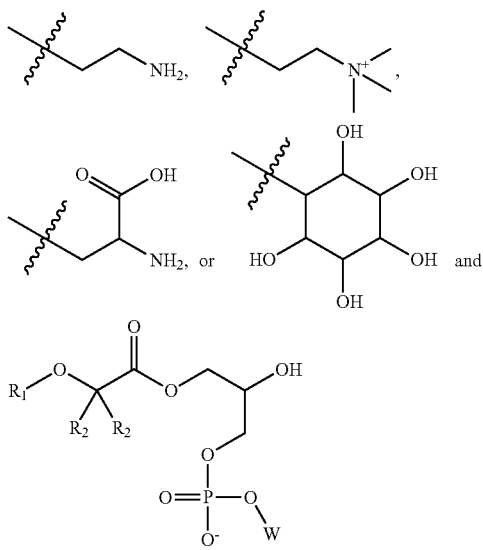
(III)
wherein W is:
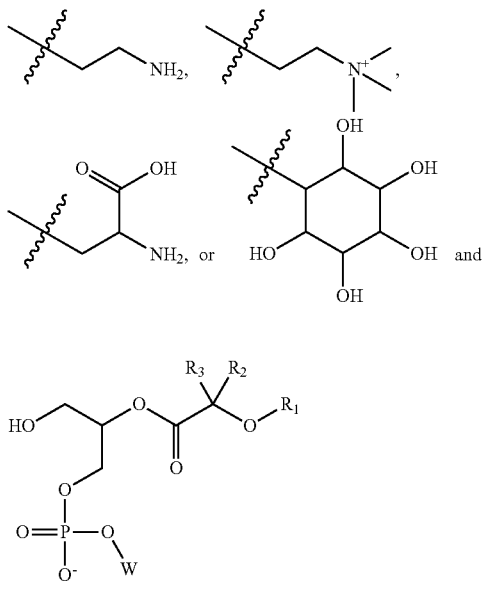
(IV)
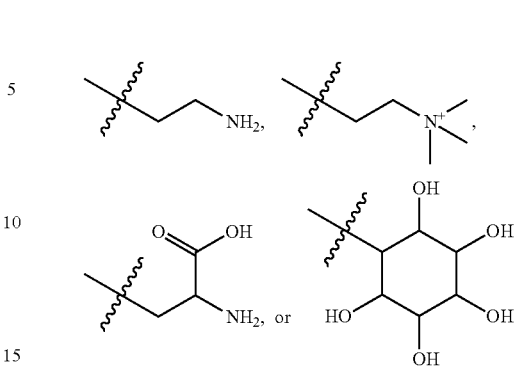
Compounds of formula (I), wherein X is a carboxylic acid in the form of a triglyceride, a 1,2-diglyceride, a 1,3 diglyceride, a 1-monoglyceride and a 2-monoglyceride, are also included within the present disclosure. These are hereinafter represented by the formulas (V), (VI), (VII), (VIII) and (IX), respectively.
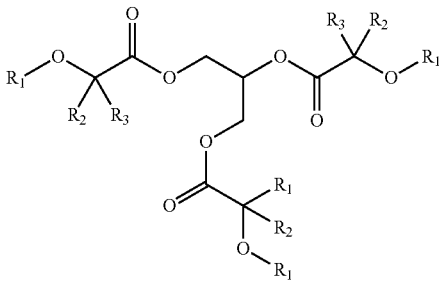
(V)
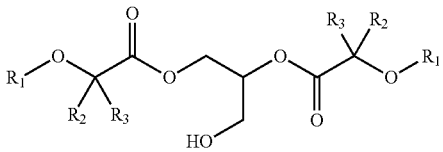
(VI)
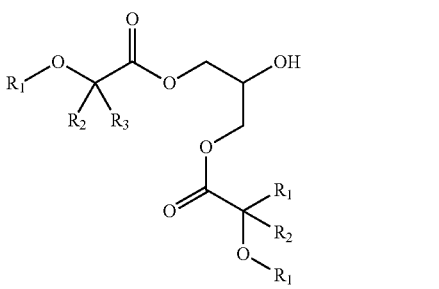
(VII)
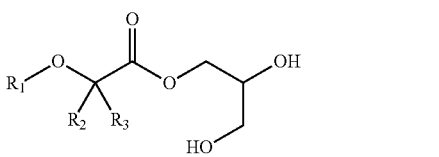
(VIII)

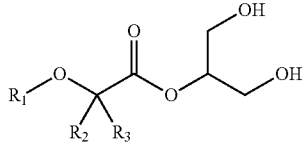
(IX)

The compounds of formula (I) are capable of existing in stereoisomeric forms. It will be understood that the invention encompasses all optical isomers of the compounds of formula (I) and mixtures thereof. Hence, compounds of formula (I) that exist as diastereomers, racemates, and enantiomers are included within the scope of the present disclosure.

The present disclosure also relates to at least one lipid compound according of formula (I) for use as a medicament.

In a further embodiment, the present disclosure provides a food supplement, a food additive, or a nutraceutical preparation comprising a lipid compound of formula (I).

Such a food supplement may be produced for administration through any route of administration. For example, the food supplement may be administered as a liquid nutritional or as a beverage.

The food supplement may be in the form of a capsule, e.g. a gelatin capsule, and the capsule may be flavoured.

In still a further embodiment, the present disclosure provides a pharmaceutical composition comprising at least one compound of formula (I), optionally together with one or more pharmaceutically acceptable carriers or excipients.

The novel lipid compounds and compositions of the disclosure may be formulated in conventional oral administration forms, e.g. tablets, coated tablets, capsules, powders, granulates, solutions, dispersions, suspensions, syrups, emulsions, and sprays, using conventional excipients, e.g. solvents, diluents, binders, sweeteners, aromas, pH modifiers, viscosity modifiers, antioxidants, corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose, or fatty substances, such as hard fat or suitable mixtures thereof. Conventional formulation techniques, well known in the art, may be used to formulate the lipid compounds according to the present disclosure.

The compositions may be administered by conventional administration routes, for example, orally. The use of orally administrable compositions, e.g. tablets, coated tablets, capsules, or syrups are included within the scope of this disclosure. For example, in some embodiments, the composition may be in the form of a gelatin capsule, a tablet, or a sachet.

A suitable daily dosage of the at least one compound according to formula (I) may range from about 1 mg to about 3 g. For example, in some embodiments, the daily dose ranges from about 1 mg to about 10 g, from about 50 mg to about 1 g, from about 10 mg to about 2 g, from about 50 mg to about 500 mg, from about 50 mg to about 200 mg, from about 100 mg to about 1 g, from about 100 mg to about 500 mg, or from about 100 mg to about 250 mg.

The pharmaceutical composition according to the present disclosure may be used as a medicament.

The present disclosure also relates to lipid compositions comprising at least one lipid compound according to formula (I). Suitably, the lipid composition may comprise at least 60% by weight, or at least 80% by weight of the at least one compound of formula (I).

The lipid composition may further comprise a pharmaceutically acceptable antioxidant, e.g. tocopherol or 3-BHA.

Further, the present disclosure relates to a lipid composition for use as a medicament.

Additionally, the present disclosure relates to the use of a lipid compound according to formula (I) for use in:
  activation or modulation of at least one of the human peroxisome proliferator-activated receptor (PPAR) isoforms α, γ or δ, wherein said compound e.g. is a pan-agonist or modulator,
  the prevention or treatment of an inflammatory condition,
  the prevention or treatment of rheumatoid arthritis,
  the prevention or treatment of inflammatory bowel disease,
  the prevention or treatment of metabolic syndrome,
  the prevention and/or treatment of a dyslipidemic condition, e.g. hypertriglyceridemia (HTG),
  the prevention and/or treatment of elevated triglyceride levels, LDL cholesterol levels, and/or VLDL cholesterol levels,
  the treatment and/or the prevention of obesity or an overweight condition,
  the reduction of body weight and/or for preventing body weight gain,
  the treatment and/or the prevention of a fatty liver disease, e.g. non-alcoholic fatty liver disease (NAFLD),
  the treatment and/or the prevention of an inflammatory disease or condition,
  the treatment and/or the prevention of atherosclerosis,
  the treatment and/or the prevention of peripheral insulin resistance and/or a diabetic condition,
  the treatment and/or prevention of type 2 diabetes, or
  the reduction of plasma insulin, blood glucose and/or serum triglycerides.

The present disclosure also relates to lipid compounds according to formula (I) for the treatment of the above mentioned conditions, and to methods for the treatment and/or prevention of the conditions listed above, comprising administering to a mammal in need thereof a pharmaceutically effective amount of a compound according to formula (I).

In addition, the present disclosure encompasses methods for manufacturing lipid compounds of formula (I). The raw material may e.g. originate from a vegetable, a microbial and/or an animal source, such as a marine fish oil. In at least one embodiment marine oil or a krill oil is used.

DETAILED DESCRIPTION

The present inventors have found that compounds of formula (I) have remarkably good pharmaceutical activity.

As used herein, the term "lipid compound" relates to fatty acid analogues derived from e.g. saturated fatty acids, monounsaturated fatty acids, polyunsaturated fatty acids and lipids comprising 1-6 triple bonds. It is to be understood that derived from includes preparation of the compounds of formula (I) from fatty acids, such as saturated fatty acids, monounsaturated fatty acids, polyunsaturated fatty acids and lipids comprising 1-6 triple bonds. Such fatty acids may occur naturally or be synthetic.

A "pharmaceutically effective amount" relates to an amount that will lead to the desired pharmacological and/or therapeutic effects, i.e. an amount of the disclosed product which is effective to achieve its intended purpose. While individual patient needs may vary, determination of optimal ranges for effective amounts of the disclosed product is within the skill of the art. Generally, the dosage regimen for treating a condition with the disclosed product of this invention is selected in accordance with a variety of factors, including the type, age, weight, sex, diet and medical condition of the patient.

By "a pharmaceutical composition" is meant a lipid compound according to the present disclosure in any form suitable to be used for a medical purpose.

"Treatment" includes any therapeutic application that can benefit a human or non-human mammal. Both human and veterinary treatments are within the scope of the present disclosure. Treatment may be in respect of an existing condition or it may be prophylactic, for example, preventative.

Fatty acids are straight chain hydrocarbons possessing a carboxyl (COOH) group at one end (α) and (usually) a methyl group at the other (ω) end. In chemistry, the numbering of the carbon atoms starts from the α end.

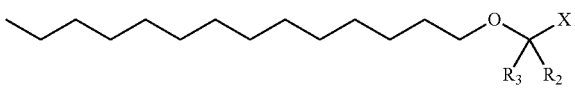

The α carbon refers to the first carbon after the carbon that attaches to the functional group, and the second carbon is the β carbon.

As used herein, the expression "methylene interrupted double bonds" relates to the case when a methylene group (—CH$_2$—) is located between two double bonds in a carbon chain of a lipid compound.

More particularly, the inventors have surprisingly found that the following lipid compound categories A-D are particularly preferable.

Category A
  derived from saturated fatty acids
  R$_1$ is a C$_{10}$-C$_{22}$ alkyl Example i

R$_1$=C$_{14}$

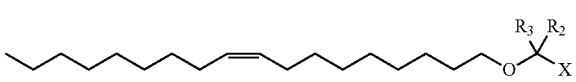

Category B
  derived from monounsaturated fatty acids
  R$_1$ is a C$_{10}$-C$_{22}$ alkenyl having 1 double bond Example ii

R$_1$=C$_{18}$

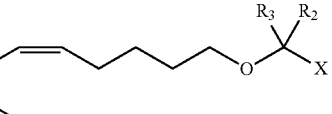

Example iii

R$_1$=C$_{14}$

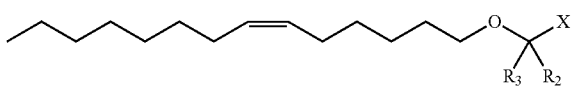

Category C:
  derived from polyunsaturated fatty acids
  R$_1$ is a C$_{20}$ alkenyl having 5 double bonds Example iv R$_1$=C$_{20}$ with 5 Methylene Interrupted Double Bonds in Z-Configuration

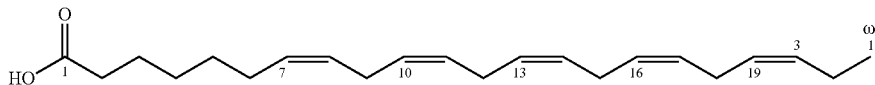

Category D:
  derived from polyunsaturated fatty acids
  R$_1$ is a C$_{22}$ alkenyl having 6 double bonds Example v R$_1$=C$_{22}$ with 6 Methylene Interrupted Double Bonds in Z-Configuration

Category E:
 derived from polyunsaturated fatty acids
 $R_1$ is a $C_{18}$ alkenyl having 3 double bonds Example vi $R_1=C_{18}$ with 3 Methylene Interrupted Double Bonds in Z-Configuration

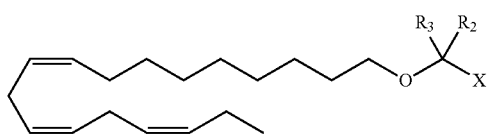

Category F:
 derived from polyunsaturated fatty acids
 $R_1$ is a $C_{15}$ alkenyl having 4 double bonds Example vii $R_1=C_{15}$ with 4 Methylene Interrupted Double Bonds in Z-Configuration

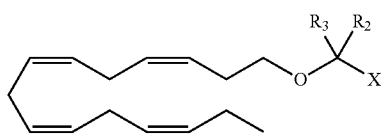

Category G:
 derived from polyunsaturated fatty acids
 $R_1$ is a $C_{18}$ alkenyl having 5 double bonds Example viii $R_1=C_{18}$ with 5 Methylene Interrupted Double Bonds in Z-Configuration

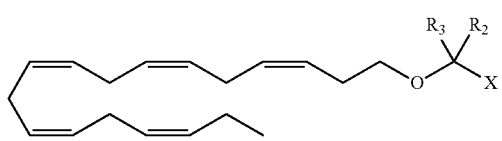

Category H:
 X is a carboxylic acid in the form of a triglyceride, diglyceride, monoglyceride or phospholipid Example ix X=a Carboxylic Acid in the Form of a Triglyceride

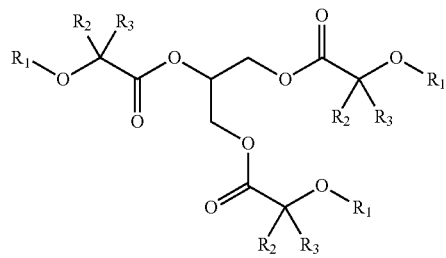

Example x

X=a Carboxylic Acid in the Form of a 2-Monoglyceride

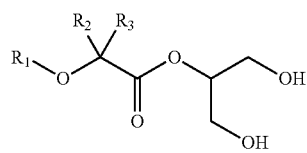

Category I
 X is a carboxylate salt

Example xi

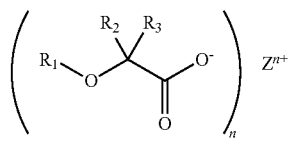

n=1 or 2
Category J
 derived from lipids comprising 1-6 triple bonds
 $R_1$ is a $C_{10}$-$C_{22}$ alkynyl Example xii $R_1=C_{14}$ with 1 Triple Bond

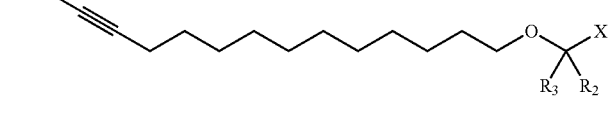

The compounds of categories A-J above, where $R_2$ and $R_3$ are different, are capable of existing in stereoisomeric forms, i.e. all optical isomers of the compounds and mixtures thereof are encompassed. Hence, the said compounds may be present as diastereomers, racemates, and enantiomers.

Specific examples of preferred lipid compounds according to the present disclosure include:

Category A:

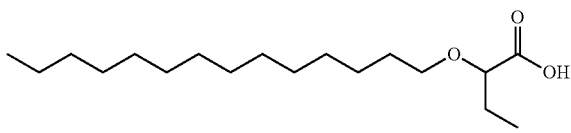 [SMILES: CCCCCCCCCCCCCCOC(CC)C(=O)O]

2-(Tetradecyloxy)butanoic acid (1)

$R_1=C_{14}H_{29}$, $R_2$=ethyl, $R_3$=H and X=COOH

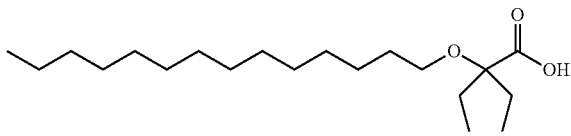 [SMILES: CCCCCCCCCCCCCCOC(CC)(CC)C(=O)O]

2-ethyl-2-(tetradecyloxy)butanoic acid (2)

$R_1=C_{14}H_{29}$, $R_2=R_3$=ethyl and X=COOH

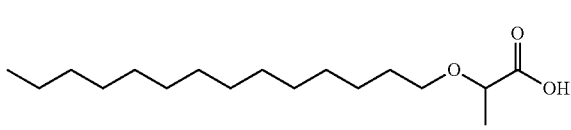 [SMILES: CCCCCCCCCCCCCCOC(C)C(=O)O]

2-(tetradecyloxy)propanoic acid (3)

$R_1=C_{14}H_{29}$, $R_2$=methyl, $R_3$=H and X=COOH

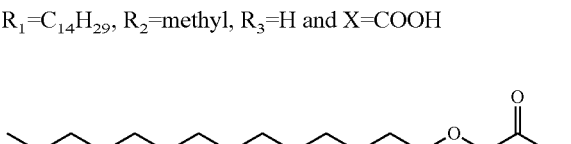

2-methyl-2-(tetradecyloxy)propanoic acid (4)

$R_1=C_{14}H_{29}$, $R_2=R_3$=methyl and X=COOH

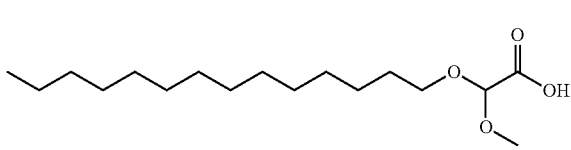 [SMILES: CCCCCCCCCCCCCCOC(OC)C(=O)O]

2-methoxy-2-(tetradecyloxy)acetic acid (5)

$R_1=C_{14}H_{29}$, $R_2$=methoxy, $R_3$=H and X=COOH

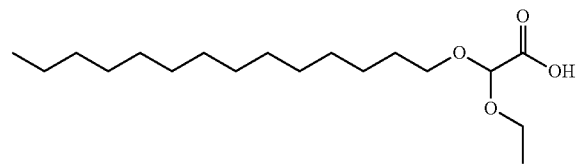 [SMILES: CCCCCCCCCCCCCCOC(OCC)C(=O)O]

2-ethoxy-2-(tetradecyloxy)acetic acid (6)

$R_1=C_{14}H_{29}$, $R_2$=ethoxy, $R_3$=H and X=COOH

Category B:

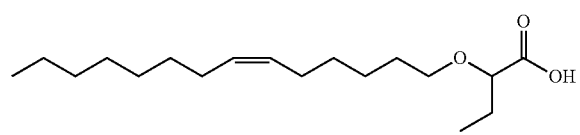 [SMILES: CCCCCCC/C=C\CCCCCOC(CC)C(=O)O]

(Z)-2-(tetradec-6-en-1-yloxy)butanoic acid (7)

$R_1=C_{14}H_{27}$, $R_2$=ethyl, $R_3$=H and X=COOH

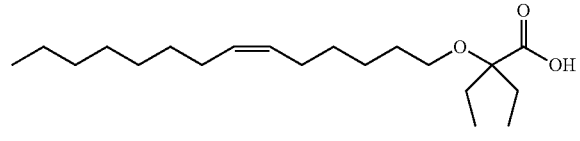 [SMILES: CCCCCCC/C=C\CCCCCOC(CC)(CC)C(=O)O]

(Z)-2-ethyl-2-(tetradec-6-en-1-yloxy)butanoic acid (8)

$R_1=C_{14}H_{27}$, $R_2=R_3$=ethyl and X=COOH

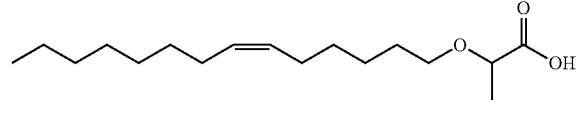 [SMILES: CCCCCCC/C=C\CCCCCOC(C)C(=O)O]

(Z)-2-(tetradec-6-en-1-yloxy)propanoic acid (9)

$R_1=C_{14}H_{27}$, $R_2$=methyl, $R_3$=H and X=COOH

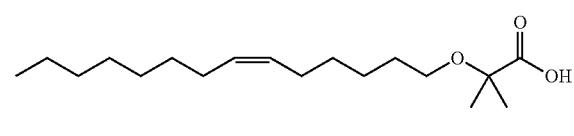 [SMILES: CCCCCCC/C=C\CCCCCOC(C)(C)C(=O)O]

15

(Z)-2-methyl-2-(tetradec-6-en-1-yloxy)propanoic acid (10)

$R_1=C_{14}H_{27}$, $R_2=R_3$=methyl and X=COOH

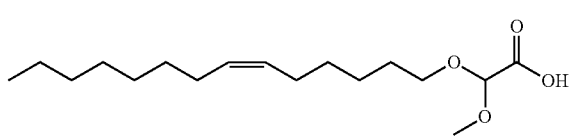 [SMILES: CCCCCCC/C=C\CCCCCOC(OC)C(=O)O]

(Z)-2-methoxy-2-(tetradec-6-en-1-yloxy)acetic acid (11)

$R_1=C_{14}H_{27}$, $R_2$=methoxy, $R_3$=H and X=COOH

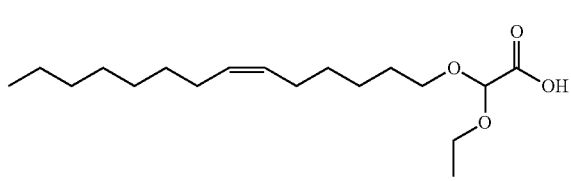 [SMILES: CCCCCCC/C=C\CCCCCOC(OCC)C(=O)O]

(Z)-2-ethoxy-2-(tetradec-6-en-1-yloxy)acetic acid (12)

$R_1=C_{14}H_{27}$, $R_2$=ethoxy, $R_3$=H and X=COOH
Category C:

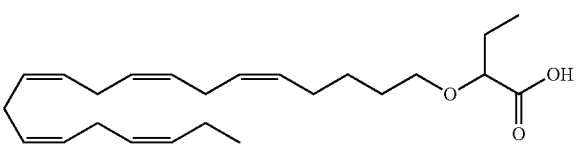

2-((5Z,8Z,11Z,14Z,17Z)-icosa-5,8,11,14,17-pentaen-1-yloxy)butanoic acid (13)

$R_1=C_{20}H_{31}$, $R_2$=ethyl, $R_3$=H and X=COOH

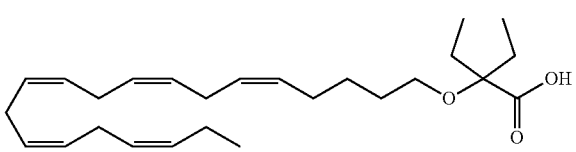 [SMILES: CC/C=C\C/C=C\C/C=C\C/C=C\C/C=C\CCCCOC(CC)(CC)C(=O)O]

16

2-ethyl-2-((5Z,8Z,11Z,14Z,17Z)-icosa-5,8,11,14,17-pentaen-1-yloxy)butanoic acid (14)

$R_1=C_{20}H_{31}$, $R_2=R_3$=ethyl and X=COOH

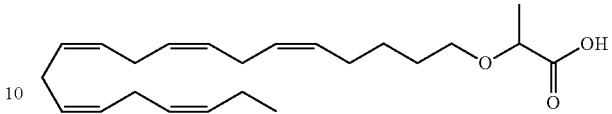

2-((5Z,8Z,11Z,14Z,17Z)-icosa-5,8,11,14,17-pentaen-1-yloxy)propanoic acid (15)

$R_1=C_{20}H_{31}$, $R_2$=methyl, $R_3$=H and X=COOH 2-((5Z,8Z,11Z,14Z,17Z)-icosa-5,8,11,14,17-pentaen-1-yloxy)-2-methylpropanoic acid (16)

$R_1=C_{20}H_{31}$, $R_2=R_3$=methyl and X=COOH

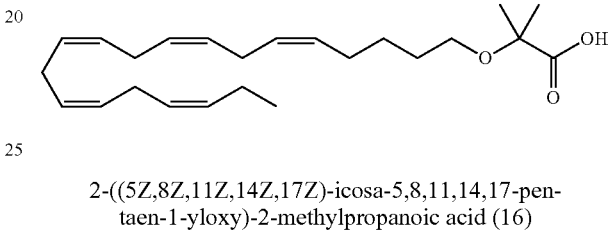

2-((5Z,8Z,11Z,14Z,17Z)-icosa-5,8,11,14,17-pentaen-1-yloxy)-2-methoxyacetic acid (17)

$R_1=C_{20}H_{31}$, $R_2$=methoxy, $R_3$=H and X=COOH

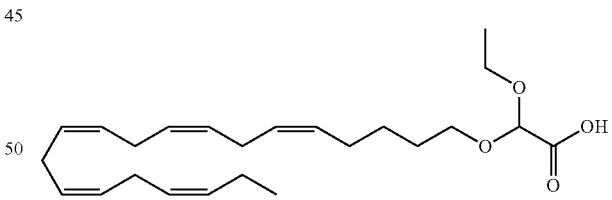

2-ethoxy-2-((5Z,8Z,11Z,14Z,17Z)-icosa-5,8,11,14,17-pentaen-1-yloxy)acetic acid (18)

$R_1=C_{20}H_{31}$, $R_2$=ethoxy, $R_3$=H and X=COOH
Category D:

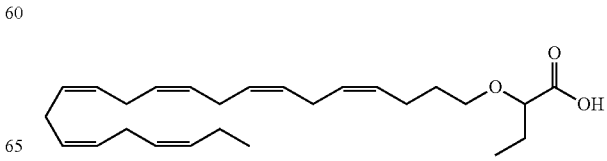

| 17 | 18 |
|---|---|
| 2-((4Z,7Z,10Z,13Z,16Z,19Z)-docosa-4,7,10,13,16,19-hexaen-1-yloxy)butanoic acid (19) | 2-((4Z,7Z,10Z,13Z,16Z,19Z)-docosa-4,7,10,13,16,19-hexaen-1-yloxy)-2-ethoxyacetic acid (24) |

$R_1=C_{22}H_{33}$, $R_2$=ethyl, $R_3$=H and X=COOH $R_1=C_{22}H_{33}$, $R_2$=ethoxy, $R_3$=H and X=COOH Category E:

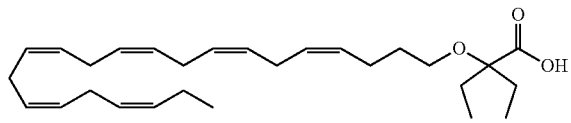 [SMILES: CC/C=C\C/C=C\C/C=C\C/C=C\C/C=C\C/C=C\CCCOC(CC)(CC)C(=O)O]

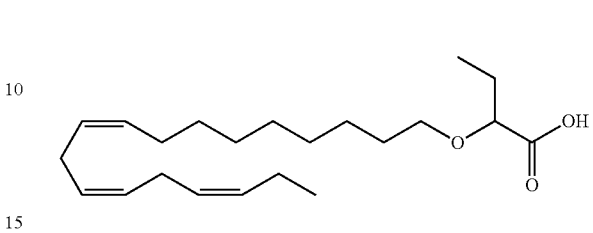

2-((4Z,7Z,10Z,13Z,16Z,19Z)-docosa-4,7,10,13,16,19-hexaen-1-yloxy)-2-ethylbutanoic acid (20)

$R_1=C_{22}H_{33}$, $R_2=R_3$=ethyl and X=COOH 2-((9Z,12Z,15Z)-octadeca-9,12,15-trien-1-yloxy)butanoic acid (25)

$R_1=C_{18}H_{31}$, $R_2$=ethyl, $R_3$=H and X=COOH

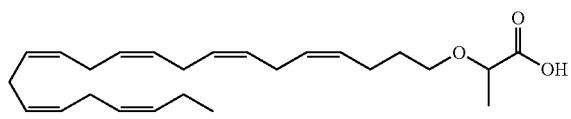

2-((4Z,7Z,10Z,13Z,16Z,19Z)-docosa-4,7,10,13,16,19-hexaen-1-yloxy)propanoic acid (21)

$R_1=C_{22}H_{33}$, $R_2$=methyl, $R_3$=H and X=COOH

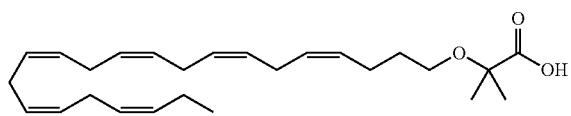 [SMILES: CC/C=C\C/C=C\C/C=C\C/C=C\C/C=C\C/C=C\CCCOC(C)(C)C(=O)O]

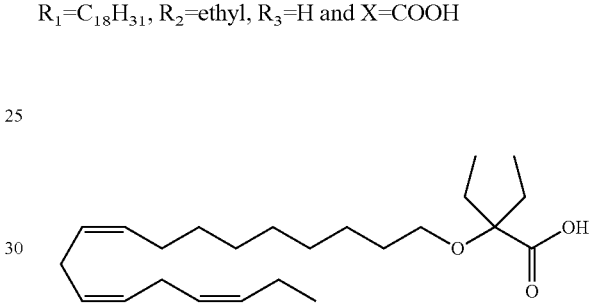

2-ethyl-2-((9Z,12Z,15Z)-octadeca-9,12,15-trien-1-yloxy)butanoic acid (26) $R_1=C_{18}H_{31}$, $R_2=R_3$=ethyl and X=COOH 2-((4Z,7Z,10Z,13Z,16Z,19Z)-docosa-4,7,10,13,16,19-hexaen-1-yloxy)-2-methylpropanoic acid (22)

$R_1=C_{22}H_{33}$, $R_2=R_3$=methyl and X=COOH

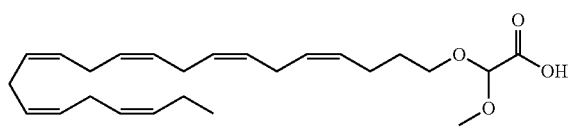

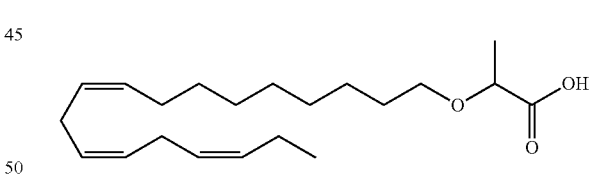

2-((4Z,7Z,10Z,13Z,16Z,19Z)-docosa-4,7,10,13,16,19-hexaen-1-yloxy)-2-methoxyacetic acid (23)

$R_1=C_{22}H_{33}$, $R_2$=methoxy, $R_3$=H and X=COOH 2-((9Z,12Z,15Z)-octadeca-9,12,15-trien-1-yloxy)propanoic acid (27)

$R_1=C_{18}H_{31}$, $R_2$=methyl, $R_3$=H and X=COOH

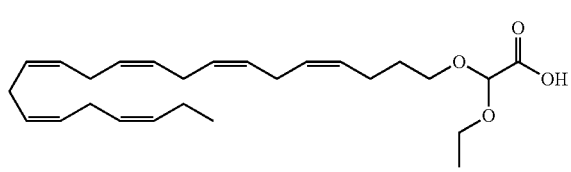 [SMILES: CC/C=C\C/C=C\C/C=C\C/C=C\C/C=C\C/C=C\CCCOC(OCC)C(=O)O]

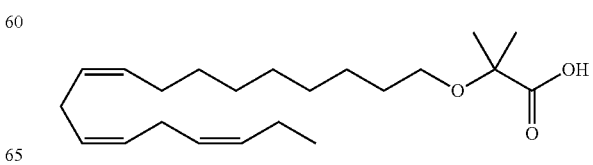

19

2-methyl-2-((9Z,12Z,15Z)-octadeca-9,12,15-trien-1-yloxy)propanoic acid (28)

$R_1=C_{18}H_{31}$, $R_2=R_3$=methyl and X=COOH

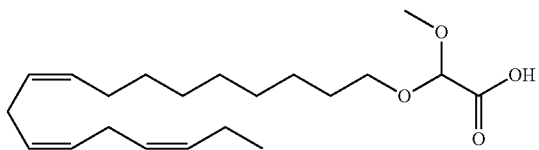 [SMILES: CC/C=C\C/C=C\C/C=C\CCCCCCCCOC(OC)C(=O)O]

2-methoxy-2-((9Z,12Z,15Z)-octadeca-9,12,15-trien-1-yloxy)acetic acid (29)

$R_1=C_{18}H_{31}$, $R_2$=methoxy, $R_3$=H and X=COOH

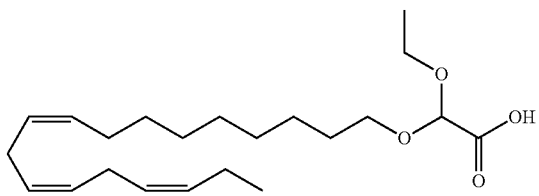 [SMILES: CC/C=C\C/C=C\C/C=C\CCCCCCCCOC(OCC)C(=O)O]

2-ethoxy-2-((9Z,12Z,15Z)-octadeca-9,12,15-trien-1-yloxy)acetic acid (30)

$R_1=C_{18}H_{31}$, $R_2$=ethoxy, $R_3$=H and X=COOH
Category F:

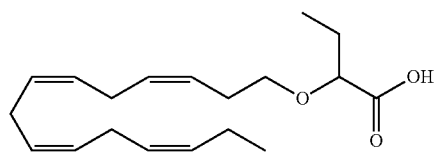 [SMILES: CC/C=C\C/C=C\C/C=C\C/C=C\CCOC(CC)C(=O)O]

2-((3Z,6Z,9Z,12Z)-pentadeca-3,6,9,12-tetraen-1-yloxy)butanoic acid (31)

$R_1=C_{15}H_{23}$, $R_2$=ethyl, $R_3$=H and X=COOH

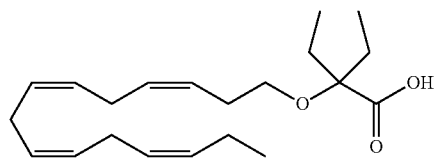 [SMILES: CC/C=C\C/C=C\C/C=C\C/C=C\CCOC(CC)(CC)C(=O)O]

20

2-ethyl-2-((3Z,6Z,9Z,12Z)-pentadeca-3,6,9,12-tetraen-1-yloxy)butanoic acid (32)

$R_1=C_{15}H_{23}$, $R_2=R_3$=ethyl and X=COOH

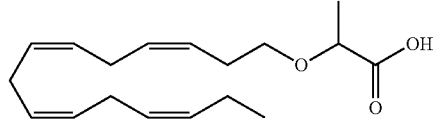 [SMILES: CC/C=C\C/C=C\C/C=C\C/C=C\CCOC(C)C(=O)O]

2-((3Z,6Z,9Z,12Z)-pentadeca-3,6,9,12-tetraen-1-yloxy)propanoic acid (33)

$R_1=C_{15}H_{23}$, $R_2$=methyl, $R_3$=H and X=COOH

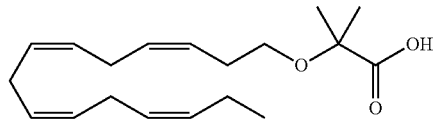 [SMILES: CC/C=C\C/C=C\C/C=C\C/C=C\CCOC(C)(C)C(=O)O]

2-methyl-2-((3Z,6Z,9Z,12Z)-pentadeca-3,6,9,12-tetraen-1-yloxy)propanoic acid (34)

$R_1=C_{15}H_{23}$, $R_2=R_3$=methyl and X=COOH

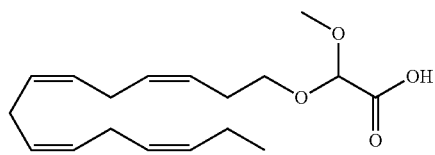 [SMILES: CC/C=C\C/C=C\C/C=C\C/C=C\CCOC(OC)C(=O)O]

2-methoxy-2-((3Z,6Z,9Z,12Z)-pentadeca-3,6,9,12-tetraen-1-yloxy)acetic acid (35)

$R_1=C_{15}H_{23}$, $R_2$=methoxy, $R_3$=H and X=COOH

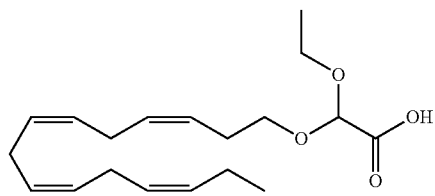 [SMILES: CC/C=C\C/C=C\C/C=C\C/C=C\CCOC(OCC)C(=O)O]

2-ethoxy-2-((3Z,6Z,9Z,12Z)-pentadeca-3,6,9,12-tetraen-1-yloxy)acetic acid (36)

$R_1=C_{15}H_{23}$, $R_2$=ethoxy, $R_3$=H and X=COOH
Category G:

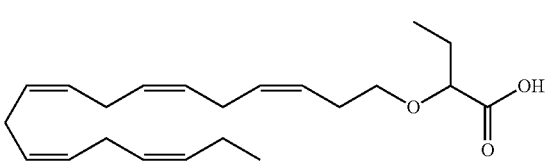 [SMILES: CC/C=C\C/C=C\C/C=C\C/C=C\C/C=C\CCOC(CC)C(=O)O]

21

2-((3Z,6Z,9Z,12Z,15Z)-octadeca-3,6,9,12,15-pentaen-1-yloxy)butanoic acid (37)

$R_1=C_{18}H_{27}$, $R_2$=ethyl, $R_3$=H and X=COOH

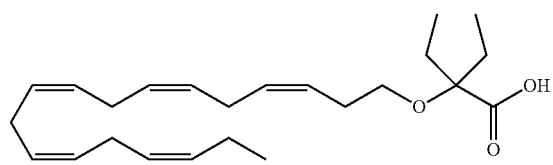 [SMILES: CC/C=C\C/C=C\C/C=C\C/C=C\C/C=C\CCOC(CC)(CC)C(=O)O]

2-ethyl-2-((3Z,6Z,9Z,12Z,15Z)-octadeca-3,6,9,12,15-pentaen-1-yloxy)butanoic acid (38)

$R_1=C_{18}H_{27}$, $R_2=R_3$=ethyl and X=COOH

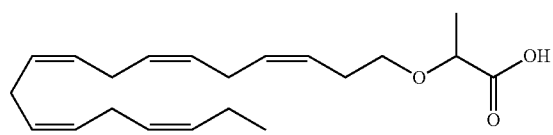 [SMILES: CC/C=C\C/C=C\C/C=C\C/C=C\C/C=C\CCOC(C)C(=O)O]

2-((3Z,6Z,9Z,12Z,15Z)-octadeca-3,6,9,12,15-pentaen-1-yloxy)propanoic acid (39)

$R_1=C_{18}H_{27}$, $R_2$=methyl, $R_3$=H and X=COOH

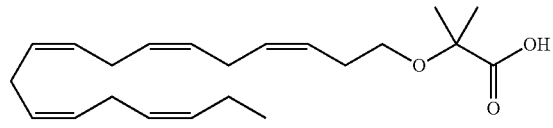 [SMILES: CC/C=C\C/C=C\C/C=C\C/C=C\C/C=C\CCOC(C)(C)C(=O)O]

22

2-methyl-2-((3Z,6Z,9Z,12Z,15Z)-octadeca-3,6,9,12,15-pentaen-1-yloxy)propanoic acid (40)

$R_1=C_{18}H_{27}$, $R_2=R_3$=methyl and X=COOH

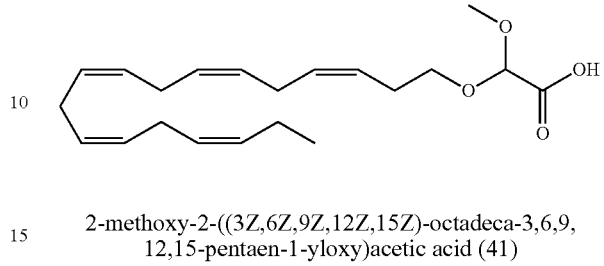

2-methoxy-2-((3Z,6Z,9Z,12Z,15Z)-octadeca-3,6,9,12,15-pentaen-1-yloxy)acetic acid (41)

$R_1=C_{18}H_{27}$, $R_2$=methoxy, $R_3$=H and X=COOH

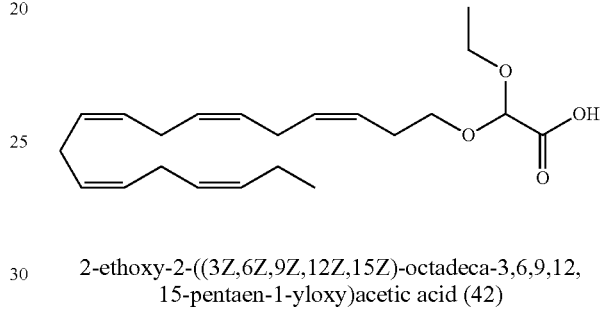

2-ethoxy-2-((3Z,6Z,9Z,12Z,15Z)-octadeca-3,6,9,12,15-pentaen-1-yloxy)acetic acid (42)

$R_1=C_{18}H_{27}$, $R_2$=ethoxy, $R_3$=H and X=COOH

Category H:

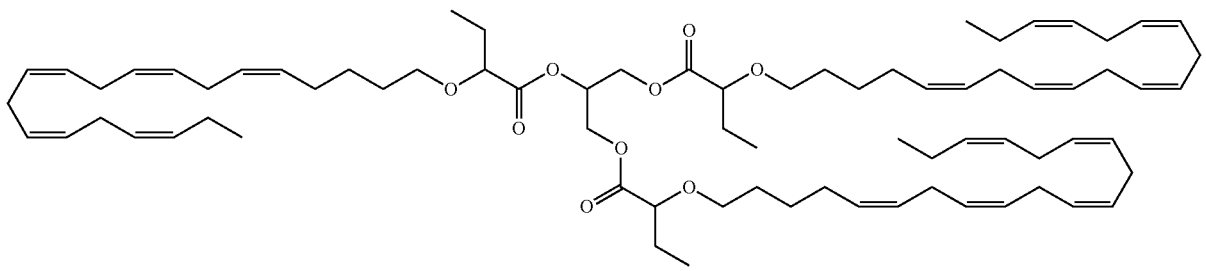 [SMILES: CC/C=C\C/C=C\C/C=C\C/C=C\C/C=C\CCCCOC(CC)C(=O)OCC(COC(=O)C(CC)OCCCC/C=C\C/C=C\C/C=C\C/C=C\C/C=C\CC)OC(=O)C(CC)OCCCC/C=C\C/C=C\C/C=C\C/C=C\C/C=C\CC]

propane-1,2,3-triyl tris(2-((5Z,8Z,11Z,14Z,17Z)-icosa-5,8,11,14,17-pentaen-1-yloxy)butanoate) (43)

$R_1=C_{20}H_{31}$, $R_2$=ethyl, $R_3$=H and X=a carboxylic acid in the form of a triglyceride

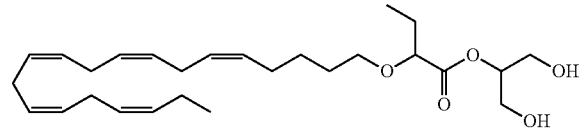 [SMILES: CC/C=C\C/C=C\C/C=C\C/C=C\C/C=C\CCCCOC(CC)C(=O)OC(CO)CO]

1,3-dihydroxypropan-2-yl 2-((5Z,8Z,11Z,14Z,17Z)-icosa-5,8,11,14,17-pentaen-1-yloxy)butanoate (44)

$R_1=C_{20}H_{31}$, $R_2$=ethyl, $R_3$=H and X=a carboxylic acid in the form of a 2-monoglyceride Category I:

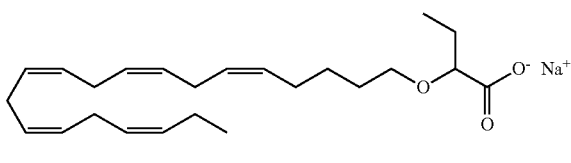

sodium 2-((5Z,8Z,11Z,14Z,17Z)-icosa-5,8,11,14,17-pentaen-1-yloxy)butanoate (45)

$R_1=C_{18}H_{31}$, $R_2$=ethyl, $R_3$=H, X=COO⁻ and $Z^+$ is $Na^+$.

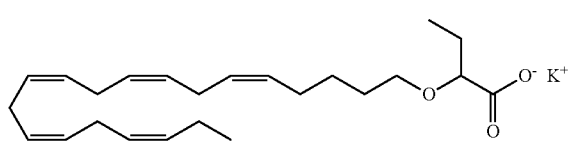

potassium 2-((5Z,8Z,11Z,14Z,17Z)-icosa-5,8,11,14,17-pentaen-1-yloxy)butanoate (46)

$R_1=C_{18}H_{31}$, $R_2$=ethyl, $R_3$=H, X=COO⁻ and $Z^+$ is K.

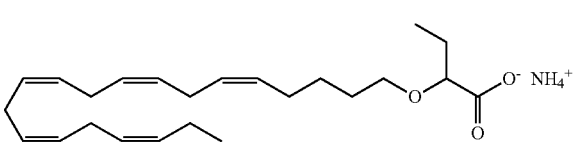 [SMILES: CC/C=C\C/C=C\C/C=C\C/C=C\C/C=C\CCCCOC(CC)C(=O)[O-] ; [NH4+]]

ammonium 2-((5Z,8Z,11Z,14Z,17Z)-icosa-5,8,11,14,17-pentaen-1-yloxy)butanoate (47)

$R_1=C_{18}H_{31}$, $R_2$=ethyl, $R_3$=H, X=COO⁻ and $Z^+$ is $NH_4^+$.

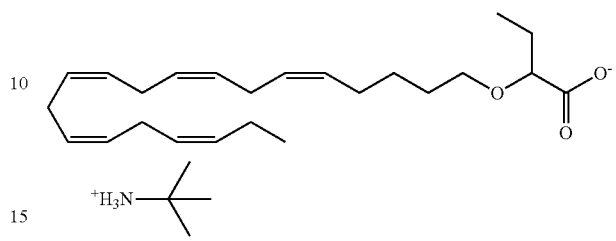

tert-butyl-ammonium 2-((5Z,8Z,11Z,14Z,17Z)-icosa-5,8,11,14,17-pentaen-1-yloxy)butanoate (48)

$R_1=C_{18}H_{31}$, $R_2$=ethyl, $R_3$=H, X=COO⁻ and $Z^+$ is tert-butyl ammonium.

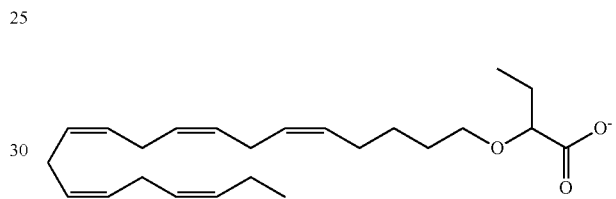

1,3-dihydroxy-2-(hydroxymethyl)propan-2-aminium 2-((5Z,8Z,11Z,14Z,17Z)-icosa-5,8,11,14,17-pentaen-1-yloxy)butanoate (49)

$R_1=C_{18}H_{31}$, $R_2$=ethyl, $R_3$=H, X=COO⁻ and $Z^+$ is 1,3-dihydroxy-2-(hydroxymethyl)propan-2-ammonium.

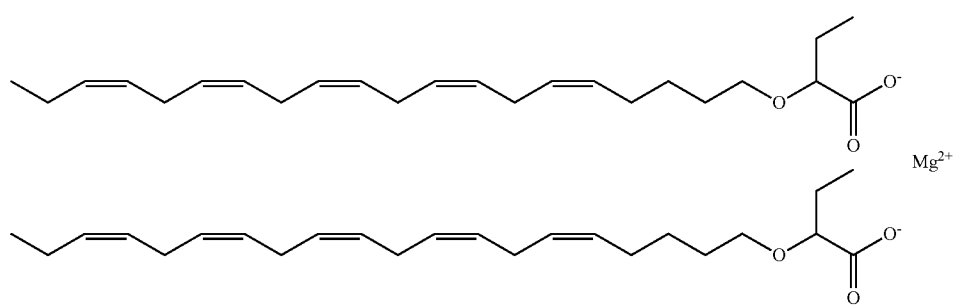

magnesium 2-((5Z,8Z,11Z,14Z,17Z)-icosa-5,8,11,
14,17-pentaen-1-yloxy)butanoate (50)

$R_1=C_{18}H_{31}$, $R_2$=ethyl, $R_3$=H, X=COO⁻ and $Z^{2+}$ is $Mg^{2+}$.

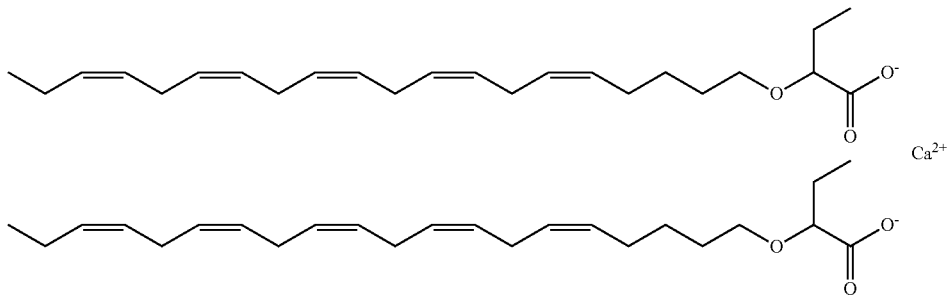 [SMILES: CC/C=C\C/C=C\C/C=C\C/C=C\C/C=C\CCCCOC(CC)C(=O)[O-] ; [Ca+2] ; CC/C=C\C/C=C\C/C=C\C/C=C\C/C=C\CCCCOC(CC)C(=O)[O-]]

calcium 2-((5Z,8Z,11Z,14Z,17Z)-icosa-5,8,11,14,
17-pentaen-1-yloxy)butanoate (51)

$R_1=C_{18}H_{31}$, $R_2$=ethyl, $R_3$=H, X=COO" and $Z^{2+}$ is $Ca^{2+}$.
Category J:

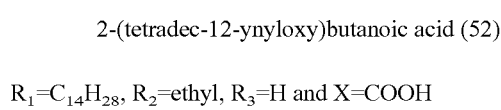

2-(tetradec-12-ynyloxy)butanoic acid (52)

$R_1=C_{14}H_{28}$, $R_2$=ethyl, $R_3$=H and X=COOH

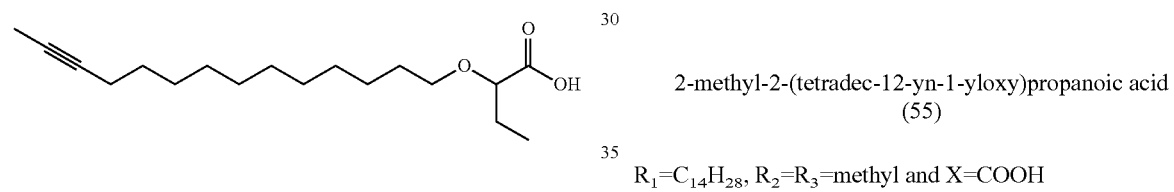

2-ethyl-2-(tetradec-12-ynyloxy)butanoic acid (53)

$R_1=C_{14}H_{28}$, $R_2=R_3$=ethyl and X=COOH

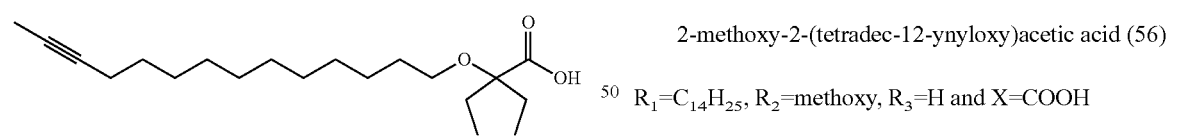

2-(tetradec-12-yn-1-yloxy)propanoic acid (54)

$R_1=C_{14}H_{28}$, $R_2$=methyl, $R_3$=H and X=COOH

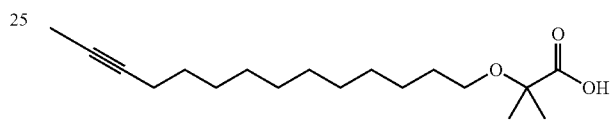

2-methyl-2-(tetradec-12-yn-1-yloxy)propanoic acid (55)

$R_1=C_{14}H_{28}$, $R_2=R_3$=methyl and X=COOH

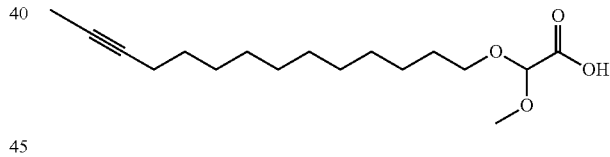

2-methoxy-2-(tetradec-12-ynyloxy)acetic acid (56)

$R_1=C_{14}H_{25}$, $R_2$=methoxy, $R_3$=H and X=COOH

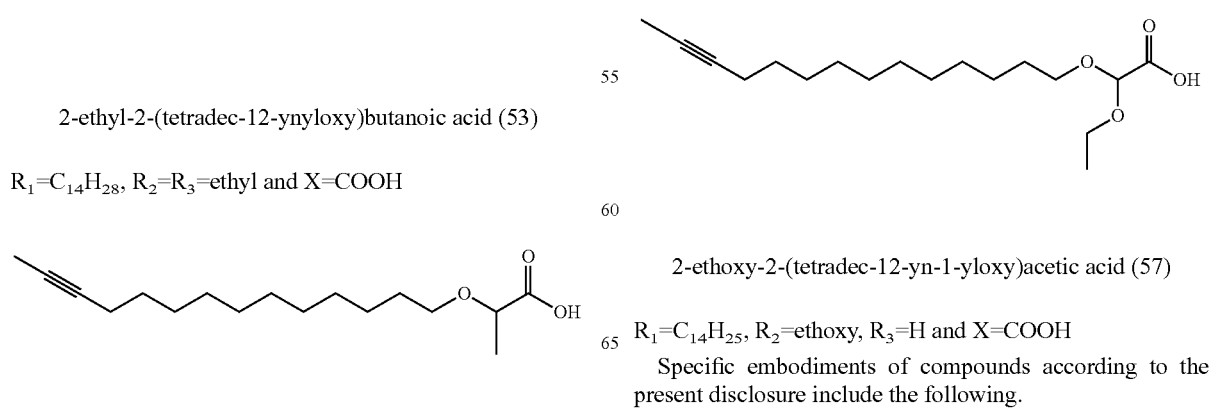

2-ethoxy-2-(tetradec-12-yn-1-yloxy)acetic acid (57)

$R_1=C_{14}H_{25}$, $R_2$=ethoxy, $R_3$=H and X=COOH

Specific embodiments of compounds according to the present disclosure include the following.

General Synthetic Methods for the Compounds Described Herein.

The compounds of general formula (I) can be prepared by the following general procedures:

Method I:

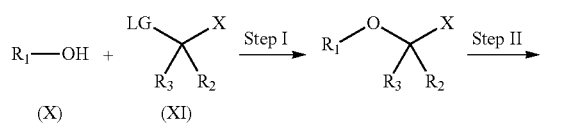

Method II:

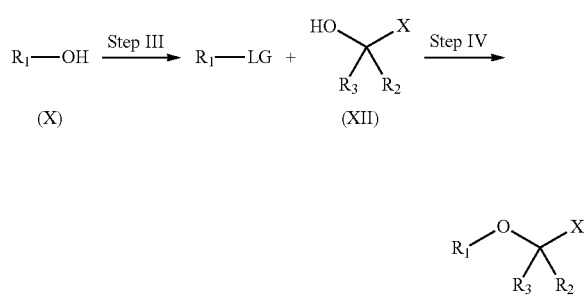

Method III:

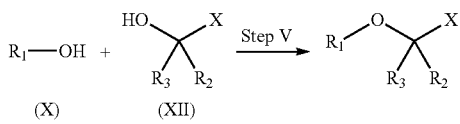

The alcohols of formula (X) described in method I, II and III may be prepared directly from the carboxylic esters of, for example, naturally occurring fatty acids; e.g. alpha-linolenic acid, conjugated linoleic acid, or eicosapentaenoic acid (EPA) by reduction with a reducing agent like lithium aluminum hydride (LAH) or diisobultyl aluminum hydride (DIBAL-H) at −10° C. to 0° C. The alcohols can also be prepared by degradation of the polyunsaturated fatty acids, such as EPA and DHA, as described by Holmeide et al. (*J. Chem. Soc., Perkin Trans.* 1 (2000) 2271.) In this case, one can start with purified EPA or DHA, but it is also possible to start with fish oil containing EPA and DHA.

Compounds of formula (XI) and (XII) are commercially available, or they are known in the literature, or they are prepared by standard processes known in the art. The leaving group (LG) present in compounds of formula (XI) may, for example, be mesylate, tosylate or a suitable halogen, such as bromine. Other leaving groups will be apparent to the skilled artisan.

Using method I, the alcohols of formula (X) can react in a substitution reaction with a compound of formula (XI) in the presence of base such as an alkali metal hydroxide, for example NaOH in an appropriate solvent system. Suitable solvent systems include a two-phase mixture of toluene and water. In those cases where R2 and/or R3 present in the compound of formula (XI) are hydrogen, an alkylation step may be added to the sequence (Step II) in order to replace one or both of these hydrogen's with an alkyl group. Such alkylation may be performed by treating the product from Step I with an alkyl group bearing a suitable leaving group, for example a halogen, such as bromine or iodine, or other leaving groups that will be apparent to a person of ordinary skill in the art, in the presence of base, such as LDA in an appropriate solvent system.

Using method II, the alcohols of formula (X) can be converted using functional group interconversion, by methods familiar to persons skilled in the art, to compounds where the terminal hydroxy group have been transformed into a suitable leaving group (LG). Suitable leaving groups include bromine, mesylate, and tosylate, or others that will be apparent to one of ordinary skill in the art. These compounds can be reacted further (step IV) in a substitution reaction with the appropriately substituted hydroxy acetic acid derivatives (compounds of formula XII), in the presence of base in an appropriate solvent system.

Using method III, the alcohol of formula (X) can react with the appropriately substituted hydroxy acetic acid derivatives (compounds of formula XII), under classic or non-classic Mitsunobu conditions, using methods familiar to persons skilled in the art.

If the acid derivatives used are carboxylic esters, hydrolysis can be performed to obtain the free fatty acids. An esterifying group such as a methyl or an ethyl group may be removed, for example, by alkaline hydrolysis using a base such as an alkali metal hydroxide, for example LiOH, NaOH or KOH or by using an organic base, for example Et$_3$N together with an inorganic salt, for example LiCl in an appropriate solvent system. A tert-butyl group may be removed, for example, by treatment with an acid, for example an organic acid such as trifluoroacetic acid or formic acid in an appropriate solvent system. Suitable solvent systems include dichloromethane. An arylmethylene group such as a benzyl group may be removed, for example, by hydrogenation over a catalyst such as palladium-on-carbon in an appropriate solvent system.

Salification of a carboxylic acid of formula (I) can be performed by treating it with a suitable base in an appropriate solvent system. Removal of the solvent will give the resulting salt.

The preparation of compounds of formula (I), according to method I, II or III, may result in mixtures of stereoisomers. If required, these isomers may be separated by means of chiral resolving agents and/or by chiral column chromatography through methods known to the person skilled in the art.

Method IV.

The compounds of formula (I) wherein X is a carboxylic acid derivative in the form of a phospholipid can be prepared through the following processes.

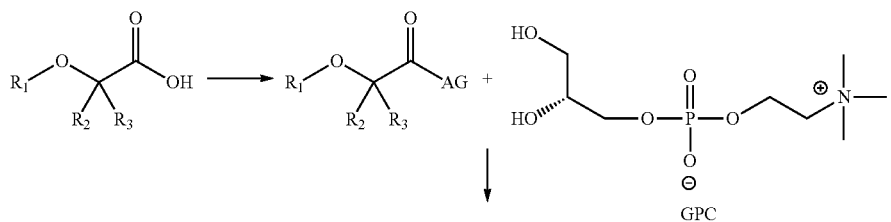

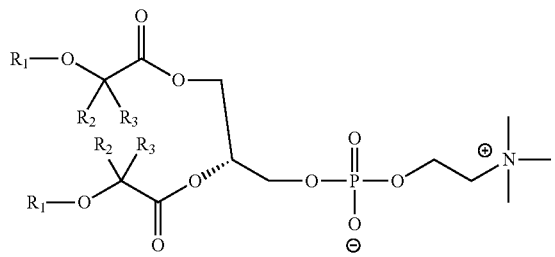

Acylation of sn-glycero-3-phosphocholine (GPC) with an activated fatty acid, such as fatty acid imidazolides, is a standard procedure in phosphatidylcholine synthesis. It is usually carried out in the presence of DMSO anion with DMSO as solvent. (Hermetter; *Chemistry and Physics of lipids*, (1981) 28, 111.) Sn-Glycero-3-phosphocholine, as a cadmium (II) adduct can also be reacted with the imidazolide activated fatty acid in the presence of DBU (1,8-diazabicyclo[5.4.0]undec-7-ene) to prepare the phosphatidylcholine of the respective fatty acid. (International application number PCT/GB2003/002582.) Enzymatic transphosphatidylation can effect the transformation of phosphatidylcholine to phosphatidyletanolamine. (Wang et al, *J. Am. Chem. Soc.*, (1993) 115, 10487.)

Phospholipids may also be prepared by enzymatic esterification and transesterification of phospholipids or enzymatic transphosphatidylation of phospholipids. (Hosokawa, *J. Am. Oil Chem. Soc.* 1995, 1287, Lilja-Hallberg, *Biocatalysis*, (1994) 195.)

Method V

The compounds of formula (I) wherein X is a carboxylic acid derivative in the form of a triglyceride can be prepared through the following process. Excess of the fatty acid can be coupled to glycerol using dimethylaminopyridine (DMAP) and 2-(1H-benzotriazol-1-yl)-N,N,N',N'-tetramethyluroniumhexafluorophosphate (HBTU).

Method VI

The compounds of formula (I) wherein X is a carboxylic acid derivative in the form of a diglyceride can be prepared by reaction of the fatty acid (2 equivalents) with glycerol (1 equivalent) in the presence of 1,3-dicyclohexylcarbondiimide (DCC) and 4-dimethylaminopyridine (DMAP).

Method VII

The compounds of formula (I) wherein X is a carboxylic acid derivative in the form of a monoglyceride can be prepared through the following processes.

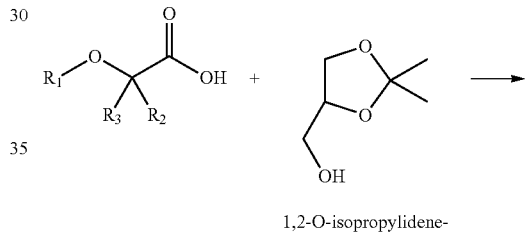

1,2-O-isopropylidene-sn-glycerol

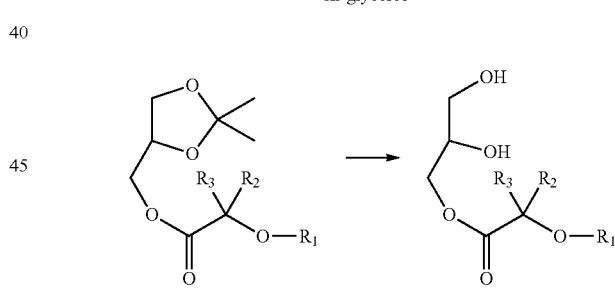

Acylation of 1,2-O-isopropylidene-sn-glycerol with a fatty acid using DCC and DMAP in chloroform gives a monodienoylglycerol. Deprotection of the isopropylidene group can be done by treating the protected glycerol with an acidic (HCl, acetic acid etc.). (O'Brian, *J. Org. Chem.*, (1996) 5914.)

There are several synthetic methods for the preparation of monoglycerides with the fatty acid in 2-position. One method utilizes esterification of the fatty acid with glycidol in the presence of 1-(3-dimethylaminopropyl)-3-ethylcarbodiimidehydrochloride (EDC) and 4-dimethylaminopyridine (DMAP) to produce a glycidyl derivative. Treatment of the glycidyl derivative with trifluoroacetic anhydride (TFAA) prior to transesterification the monoglyceride is obtained (Parkkari et al, *Bioorg. Med. Chem. Lett.* (2006) 2437.)

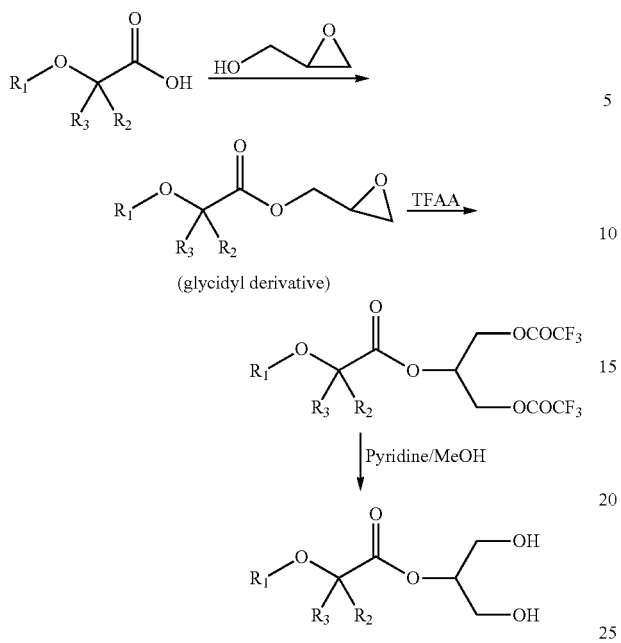

(glycidyl derivative)

Further methods for the preparation of mono-, di- and tri-glycerides of fatty acid derivatives are described in international Application No. PCT/FR02/02831.

It is also possible to use enzymatic processes (lipase reactions) for the transformation of a fatty acid to a mono-, di-, tri-glyceride. A 1,3-regiospecific lipase from the fungus *Mucor miehei* can be used to produce triglycerides or diglycerides from polyunsaturated fatty acids and glycerol. A different lipase, the non-regiospecific yeast lipase from *Candida antartica* is highly efficient in generating triglycerides from polyunsaturated fatty acids. (Haraldsson, *Pharmazie*, (2000) 3.)

Preparation, Characterization and Biological Testing of Specific Fatty Acid Derivatives of Formula (I)

Examples

The disclosure will now be further described by the following non-limiting examples, in which standard techniques known to the skilled chemist and techniques analogous to those described in these examples may be used where appropriate. Unless otherwise stated:
- evaporations were carried out by rotary evaporation in vacuo;
- all reactions were carried out at room temperature, typically in the range between 18-25° C. with solvents of HPLC grade under anhydrous conditions;
- column chromatography was performed by the flash procedure on silica gel 40-63 μm (Merck) or by an Armen Spotflash using the pre-packed silica gel columns "MiniVarioFlash", "SuperVarioFlash", "SuperVarioPrep" or "EasyVarioPrep" (Merck);
- yields are given for illustration only and are not necessarily the maximum attainable;
- the nuclear magnetic resonance (NMR) shift values were recorded on a Bruker Avance DPX 200 or 300 instrument, and the peak multiplicities are shown as follows: s, singlet; d, doublet; dd, double doublet; t, triplet; q, quartet; p, pentet; m, multiplett; br, broad;
- the mass spectra were recorded with a LC/MS spectrometer. Separation was performed using a Agilent 1100 series module on a Eclipse XDB-C18 2.1×150 mm column with gradient elution. As eluent were used a gradient of 5-95% acetonitrile in buffers containing 0.01% trifluoroacetic acid or 0.005% sodium formate. The mass spectra were recorded with a G 1956 A mass spectrometer (electrospray, 3000 V) switching positive and negative ionization mode.

Example 1

Preparation of tert-butyl 2-((5Z,8Z,11Z,14Z,17Z)-icosa-5,8,11,14,17-pentaen-1-yloxy)butanoate

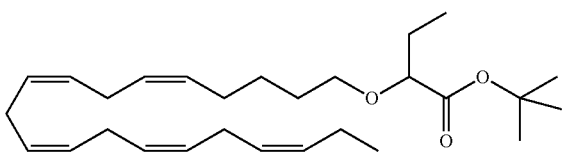 [SMILES: CC/C=C\C/C=C\C/C=C\C/C=C\C/C=C\CCCCOC(CC)C(=O)OC(C)(C)C]

Tetrabutylammonium chloride (0.55 g, 1.98 mmol) was added to a solution of (5Z,8Z,11Z,14Z,17Z)-icosa-5,8,11,14, 17-pentaen-1-ol, (3.50 g, 12.1 mmol) in toluene (35 mL) at ambient temperature under nitrogen. An aqueous solution of sodium hydroxide (50% (w/w), 11.7 mL) was added under vigorous stirring at room temperature, followed by t-butyl 2-bromobutyrate (5.41 g, 24.3 mmol). The resulting mixture was heated to 50° C. and additional t-butyl 2-bromobutyrate was added after 1.5 hours (2.70 g, 12.1 mmol), 3.5 hours (2.70 g, 12.1 mmol) and 4.5 hours (2.70 g, 12.1 mmol) and stirred for 12 hours in total. After cooling to room temperature, ice water (25 mL) was added and the resulting two phases were separated. The organic phase was washed with a mixture of NaOH (5%) and brine, dried (MgSO$_4$), filtered and concentrated. The residue was purified by flash chromatography on silica gel using increasingly polar mixtures of heptane and ethyl acetate (100:0→95:5) as eluent. Concentration of the appropriate fractions afforded 1.87 g (36% yield) of the title compound as an oil. $^1$H NMR (300 MHz, CDCl3): δ 0.85-1.10 (m, 6H), 1.35-1.54 (m, 11H), 1.53-1.87 (m, 4H), 1.96-2.26 (m, 4H), 2.70-3.02 (m, 8H), 3.31 (dt, 1H), 3.51-3.67 (m, 2H), 5.10-5.58 (m, 10H).

Example 2

Preparation of 2-((5Z,8Z,11Z,14Z,17Z)-icosa-5,8,11, 14,17-pentaenyloxy)butanoic acid

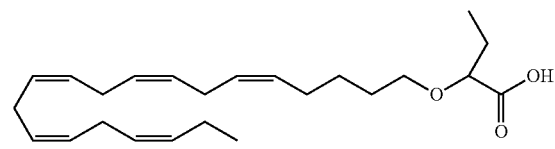 [SMILES: CC/C=C\C/C=C\C/C=C\C/C=C\C/C=C\CCCCOC(CC)C(=O)O]

tert-Butyl 2-((5Z,8Z,11Z,14Z,17Z)-icosa-5,8,11,14,17-pentaen-1-yloxy)butanoate (19.6 g, 45.5 mmol) was dissolved in dichloromethane (200 mL) and placed under nitrogen. Trifluoroacetic acid (50 mL) was added and the reaction mixture was stirred at room temperature for one hour. Water was added and the aqueous phase was extracted twice with dichloromethane. The combined organic extract was washed with brine, dried (Na$_2$SO$_4$), filtered and concentrated. The residue was subjected to flash chromatography on silica gel using increasingly polar mixtures of heptane, ethyl acetate and formic acid (90:10:1→80:20:1) as eluent. Concentration of the appropriate fractions afforded 12.1 g (71% yield) of the title compound as an oil. $^1$H-NMR (300 MHz, CDCl$_3$): ~0.90-1.00 (m, 6H), 1.50 (m, 2H), 1.70 (m, 2H), 1.80 (m, 2H), 2.10 (m, 4H), 2.80-2.90 (m, 8H), 3.50 (m, 1H), 3.60 (m, 1H), 3.75 (t, 1H), 5.30-5.50 (m, 10H); MS (electro spray): 373.2 [M−H]$^-$.

Example 3

Preparation of (4S,5R)-3-((S)-2-((5Z,8Z,11Z,14Z, 17Z)-icosa-5,8,11,14,17-pentaenyloxy)butanoyl)-4-methyl-5-phenyloxazolidin-2-one and (4S,5R)-3-((R)-2-((5Z,8Z,11Z,14Z,17Z)-icosa-5,8,11,14,17-pentaenyloxy)butanoyl)-4-methyl-5-phenyloxazolidin-2-one

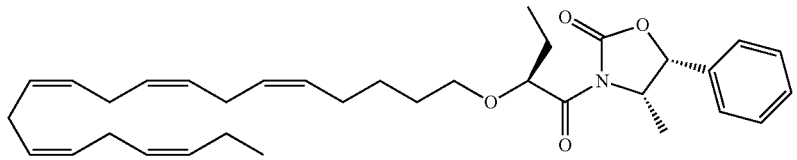

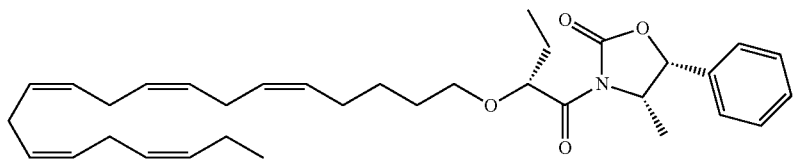

DMAP (1.10 g, 8.90 mmol) and DCC (1.90 g, 9.30 mmol) were added to a mixture of 2-((5Z,8Z,11Z,14Z,17Z)-icosa-5,8,11,14,17-pentaenyloxy)butanoic acid (3.20 g, 8.50 mmol) in dry dichloromethane (100 mL) held at 0° C. under nitrogen. The resulting mixture was stirred at 0° C. for 20 minutes. (4S,5R)-4-methyl-5-phenyloxazolidin-2-one (1.50 g, 8.50 mmol) was added and the resulting turbid mixture was stirred at ambient temperature for five days. The mixture was filtrated and concentrated under reduced pressure to give a crude product containing the desired product as a mixture of two diastereomers. The residue was purified by flash chromatography on silica gel using 15% ethyl acetate in heptane as eluent. The two diastereomers were separated and the appropriate fractions were concentrated. (4S,5R)-3-((S)-2-((5Z,8Z,11Z,14Z,17Z)-icosa-5,8,11,14,17-pentaenyloxy)butanoyl)-4-methyl-5-phenyloxazolidin-2-one eluted first and was obtained in 1.1 g (40% yield) as an oil. (4S,5R)-3-((R)-2-((5Z,8Z,11Z,14Z,17Z)-icosa-5,8,11,14,17-pentaenyloxy)butanoyl)-4-methyl-5-phenyloxazolidin-2-one was obtained in 0.95 g (34% yield) as an oil.

(4S,5R)-3-((S)-2-((5Z,8Z,11Z,14Z,17Z)-icosa-5,8, 11,14,17-pentaenyloxy)butanoyl)-4-methyl-5-phenyloxazolidin-2-one (E1)

$^1$H-NMR (300 MHz, CDCl$_3$): δ 0.90 (d, 3H), 1.00 (t, 3H), 1.07 (t, 3H), 1.45-1.57 (m, 2H), 1.62-1.76 (m, 3H), 1.85-1.95 (m, 1H), 2.05-2.15 (m, 4H), 2.87 (m, 8H), 3.39 (m, 1H), 3.57 (m, 1H), 4.85-4.92 (m, 2H), 5.30-5.45 (m, 10H), 5.75 (d, 1H), 7.32 (m, 2H), 7.43 (m, 3H).

(4S,5R)-3-((R)-2-((5Z,8Z,11Z,14Z,17Z)-icosa-5,8, 11,14,17-pentaenyloxy)butanoyl)-4-methyl-5-phenyloxazolidin-2-one (E2)

$^1$H-NMR (300 MHz, CDCl$_3$): δ 0.98 (d, 3H), 0.99 (t, 3H), 1.08 (t, 3H), 1.40-1.52 (m, 2H), 1.55-1.75 (m, 3H), 1.80-1.90 (m, 1H), 2.05-2.15 (m, 4H), 2.84 (m, 8H), 3.39 (m, 1H), 3.56 (m, 1H), 4.79 (pent, 1H), 4.97 (dd, 1H), 5.30-5.45 (m, 10H), 5.71 (d, 1H), 7.33 (m, 2H), 7.43 (m, 3H).

Example 4

Preparation of (S)-2-((5Z,8Z,11Z,14Z,17Z)-icosa-5, 8,11,14,17-pentaenyloxy)butanoic acid

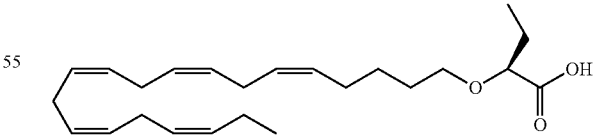

Hydrogen peroxide (35% in water, 0.75 mL, 8.54 mmol) and lithium hydroxide monohydrate (0.18 g, 4.27 mmol) was added to a solution of (4S,5R)-3-((S)-2-((5Z,8Z,11Z,14Z, 17Z)-icosa-5,8,11,14,17-pentaenyloxy)butanoyl)-4-methyl-5-phenyloxazolidin-2-one (1.10 g, 2.13 mmol) in tetrahydrofuran (12 mL) and water (4 mL) held at 0° C. under nitrogen. The reaction mixture was stirred at 0° C. for 30 minutes. 10% Na$_2$SO$_{3(aq)}$ (30 mL) was added, the pH was adjusted to ~2 with 2M HCl and the mixture was extracted twice with heptane (30 mL). The combined organic extract was dried (Na₂SO₄), filtered and concentrated. The residue was subjected to flash chromatography on silica gel using increasingly polar mixtures of heptane and ethyl acetate (98:8→1:1) as eluent. Concentration of the appropriate fractions afforded 0.48 g (60% yield) of the title compound as an oil. ¹H-NMR (300 MHz, CDCl₃): δ 0.90-1.00 (m, 6H), 1.48 (m, 2H), 1.65 (m, 2H), 1.85 (m, 2H), 2.10 (m, 4H), 2.80-2.90 (m, 8H), 3.55 (m, 1H), 3.60 (m, 1H), 3.88 (t, 1H), 5.35-5.45 (m, 10H); MS (electro spray): 373.3 [M−H]⁻; [α]_D+37° (c=0.104, ethanol)

Example 5

Preparation of (R)-2-((5Z,8Z,11Z,14Z,17Z)-icosa-5,8,11,14,17-pentaenyloxy)butanoic acid

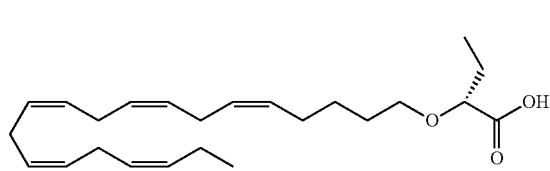 [SMILES: CC/C=C\C/C=C\C/C=C\C/C=C\C/C=C\CCCCO[C@H](CC)C(=O)O]

Hydrogen peroxide (35% in water, 0.65 mL, 7.37 mmol) and lithium hydroxide monohydrate (0.15 g, 3.69 mmol) was added to a solution of (4S,5R)-3-((R)-2-((5Z,8Z,11Z,14Z,17Z)-icosa-5,8,11,14,17-pentaenyloxy)butanoyl)-4-methyl-5-phenyloxazolidin-2-one (0.95 g, 1.84 mmol) in tetrahydrofuran (12 mL) and water (4 mL) held at 0° C. under nitrogen. The reaction mixture was stirred at 0° C. for 30 minutes. 10% Na₂SO₃(aq)(30 mL) was added, the pH was adjusted to ~2 with 2M HCl and the mixture was extracted twice with heptane (30 mL). The combined organic extract was dried (Na₂SO₄), filtered and concentrated. The residue was subjected to flash chromatography on silica gel using increasingly polar mixtures of heptane and ethyl acetate (98:8→50:50) as eluent. Concentration of the appropriate fractions afforded 0.19 g (29% yield) of the title compound as an oil. ¹H-NMR (300 MHz, CDCl₃): δ 0.90-1.00 (m, 6H), 1.48 (m, 2H), 1.65 (m, 2H), 1.85 (m, 2H), 2.10 (m, 4H), 2.80-2.90 (m, 8H), 3.55 (m, 1H), 3.60 (m, 1H), 3.88 (t, 1H), 5.35-5.45 (m, 10H); MS (electro spray): 373.3 [M−H]⁻; [α]_D−31° (c=0.088, ethanol)

Example 6

Preparation of tert-butyl 2-((5Z,8Z,11Z,14Z,17Z)-icosa-5,8,11,14,17-pentaenyloxy)propanoate

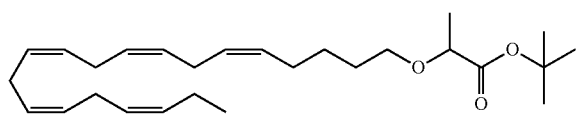 [SMILES: CC/C=C\C/C=C\C/C=C\C/C=C\C/C=C\CCCCOC(C)C(=O)OC(C)(C)C]

A mixture of (5Z,8Z,11Z,14Z,17Z)-icosa-5,8,11,14,17-pentaen-1-ol, (1.00 g, 3.47 mmol), tetrabutylammonium chloride (0.24 g, 0.87 mmol) and t-butyl α-bromo propionate (3.62 g, 17.3 mmol) was dissolved in toluene (36 mL) and placed under nitrogen. An aqueous solution of sodium hydroxide (50%, 8 mL) was added slowly under vigorous stirring and the resulting mixture was stirred at ambient temperature for twenty hours. Water was added and the mixture was extracted three times with ether. The combined organic extract was washed with brine, dried (Na₂SO₄), filtered and concentrated. The residue was purified by flash chromatography on silica gel using 2% ethyl acetate in heptane as eluent. Concentration of the appropriate fractions afforded 1.40 g (90% yield) of the title compound as an oil. ¹H-NMR (300 MHz, CDCl₃): δ 0.95 (t, 3H), 1.41 (d, 3H), 1.48 (s, 9H), 1.48-1.66 (m, 4H), 2.05 (m, 4H), 2.83 (m, 8H), 3.35 (m, 1H), 3.55 (m, 1H), 3.79 (q, 1H), 5.32-5.44 (m, 10H).

Example 7

Preparation of 2-((5Z,8Z,11Z,14Z,17Z)-icosa-5,8,11,14,17-pentaenyloxy)propanoic acid

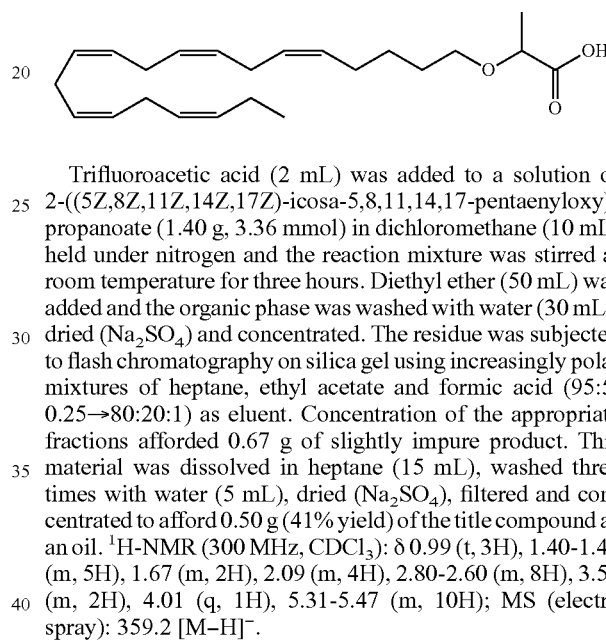

Trifluoroacetic acid (2 mL) was added to a solution of 2-((5Z,8Z,11Z,14Z,17Z)-icosa-5,8,11,14,17-pentaenyloxy) propanoate (1.40 g, 3.36 mmol) in dichloromethane (10 mL) held under nitrogen and the reaction mixture was stirred at room temperature for three hours. Diethyl ether (50 mL) was added and the organic phase was washed with water (30 mL), dried (Na₂SO₄) and concentrated. The residue was subjected to flash chromatography on silica gel using increasingly polar mixtures of heptane, ethyl acetate and formic acid (95:5:0.25→80:20:1) as eluent. Concentration of the appropriate fractions afforded 0.67 g of slightly impure product. This material was dissolved in heptane (15 mL), washed three times with water (5 mL), dried (Na₂SO₄), filtered and concentrated to afford 0.50 g (41% yield) of the title compound as an oil. ¹H-NMR (300 MHz, CDCl₃): δ 0.99 (t, 3H), 1.40-1.48 (m, 5H), 1.67 (m, 2H), 2.09 (m, 4H), 2.80-2.60 (m, 8H), 3.53 (m, 2H), 4.01 (q, 1H), 5.31-5.47 (m, 10H); MS (electro spray): 359.2 [M−H]⁻.

Example 8

Preparation of tert-butyl 2-((5Z,8Z,11Z,14Z,17Z)-icosa-5,8,11,14,17-pentaenyloxy)-2-methylpropanoate

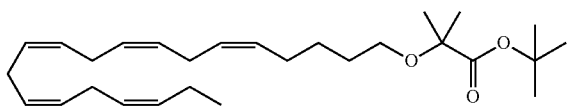 [SMILES: CC/C=C\C/C=C\C/C=C\C/C=C\C/C=C\CCCCOC(C)(C)C(=O)OC(C)(C)C]

A mixture of (5Z,8Z,11Z,14Z,17Z)-icosa-5,8,11,14,17-pentaen-1-ol, (0.83 g, 3.14 mmol), tetrabutylammonium chloride (0.24 g, 0.85 mmol) and t-butyl α-bromo isobutyrate (3.50 g, 15.7 mmol) was dissolved in toluene (15 mL) and placed under nitrogen. An aqueous solution of sodium hydroxide (50%, 5 mL) was added slowly under vigorous stirring at room temperature. The resulting mixture was heated to 60° C. and stirred for six hours. The mixture was cooled, added water and extracted three times with ether. The combined organic extract was washed with brine, dried (Na₂SO₄), filtered and concentrated. The residue was purified by flash chromatography on silica gel using a gradient of

Example 9

Preparation of 2-((5Z,8Z,11Z,14Z,17Z)-icosa-5,8,11,14,17-pentaenyloxy)-2-methylpropanoic acid

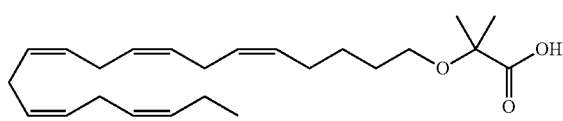

Trifluoroacetic acid (5 mL) was added to a solution of tert-butyl 2-((5Z,8Z,11Z,14Z,17Z)-icosa-5,8,11,14,17-pentaenyloxy)-2-methylpropanoate (600 mg, 1.39 mmol) in dichloromethane (20 mL) under nitrogen and the reaction mixture was stirred at room temperature for two hours. Water was added and the aqueous phase was extracted twice with dichloromethane. The combined organic extract was washed with brine, dried (Na$_2$SO$_4$), filtered and concentrated. The residue was purified by flash chromatography on silica gel using a mixture of heptane, ethyl acetate and formic acid (80:20:1) as eluent. The appropriate fractions were concentrated and the residue (135 mg) was purified further by flash chromatography on silica gel using a gradient of 5-10% of a mixture of ethyl acetate and formic acid (95:5) in heptane as eluent. Concentration of the appropriate fractions afforded 80 mg slightly impure product. This material was dissolved in heptane (5 mL), washed twice with water (5 mL), dried (Na$_2$SO$_4$), filtered and concentrated to afford 40 mg (8% yield) of the title compound as an oil. $^1$H-NMR (300 MHz, CDCl$_3$): δ 0.99 (t, 3H), 1.47 (s, 6H), 1.64 (m, 2H), 2.07 (m, 4H), 2.81-2.88 (m, 8H), 3.46 (t, 2H), 5.29-5.44 (m, 10H); MS (electro spray): 373.3 [M–H]$^-$

Example 10

Preparation of 2-((3Z,6Z,9Z,12Z)-pentadeca-3,6,9,12-tetraenyloxy)butanoic acid

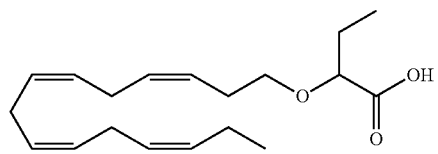

A mixture of (3Z,6Z,9Z,12Z)-pentadeca-3,6,9,12-tetraen-1-ol (S. Flock, Acta Chemica Scandinavica, (1999) 53, 436-445) (0.22 g, 1.00 mmol), tetrabutyl ammonium chloride (0.10 g, 0.33 mmol) and t-butyl 2-bromobutyrate (1.11 g, 5.00 mmol) was dissolved in toluene (10 ml) and placed under nitrogen. An aqueous solution of sodium hydroxide (50%, 4 ml) was added slowly under vigorous stirring at room temperature. The resulting mixture was heated to 50° C. and stirred for two hours and then at ambient temperature over night. After cooling to room temperature, water was added and the aqueous phase was extracted three times with ether. The combined organic extract was washed with water and brine, dried (Na$_2$SO$_4$), filtered and concentrated. The residue was purified by flash chromatography on silica gel using 5% ethyl acetate in heptane as eluent. Concentration of the appropriate fractions afforded 0.30 g of the t-butyl ester as an oil. The residue was dissolved in dichloromethane (10 mL) and placed under nitrogen. Trifluoroacetic acid (2 mL) was added and the reaction mixture was stirred at room temperature for one hour. Water was added and the aqueous phase was extracted twice with dichloromethane. The combined organic extract was washed with brine, dried (Na$_2$SO$_4$), filtered and concentrated. The residue was purified by flash chromatography on silica gel using a mixture of heptane, ethyl acetate and formic acid (80:20:1) as eluent. Concentration of the appropriate fractions afforded 0.18 g (59% yield) of the desired product as an oil. $^1$H-NMR (300 MHz, CDCl$_3$): δ 0.90-1.05 (m, 6H), 1.75-1.90 (m, 2H), 2.05-2.15 (m, 2H), 2.30-2.50 (m, 2H), 2.85 (m, 6H), 3.60 (m, 2H), 3.85 (t, 1H), 5.25-5.60 (m, 8H).

Example 11

Preparation of 2-((9Z,12Z,15Z)-octadeca-9,12,15-trienyloxy)butanoic acid

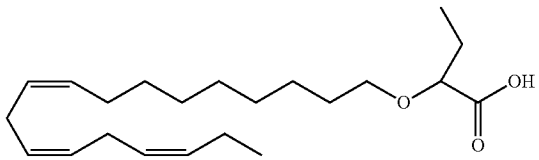 [SMILES: CC/C=C\C/C=C\C/C=C\CCCCCCCCOC(CC)C(=O)O]

A mixture of (9Z,12Z,15Z)-octadeca-9,12,15-trien-1-ol (1.26 g, 4.76 mmol), tetra-butyl ammonium chloride (0.36 g, 1.28 mmol) and t-butyl 2-bromobutyrate (2.86 g, 12.82 mol) was dissolved in toluene (15 mL) and placed under nitrogen. An aqueous solution of sodium hydroxide (50%, 6 mL) was added slowly under vigorous stirring at room temperature. The resulting mixture was heated to 60° C. and stirred for five hours. After cooling to room temperature, water was added and the aqueous phase was extracted three times with ether. The combined organic extract was washed with water and brine, dried (Na$_2$SO$_4$), filtered and concentrated. The residue was purified by flash chromatography on silica gel using a gradient of 2.5-5% ethyl acetate in heptane as eluent. Concentration of the appropriate fractions afforded 1.36 g of the t-butyl ester as an oil. The residue was dissolved in dichloromethane (20 mL) and placed under nitrogen. Trifluoroacetic acid (5 mL) was added and the reaction mixture was stirred at room temperature for one hour. Water was added and the aqueous phase was extracted twice with dichloromethane. The combined organic extract was washed with brine, dried (Na$_2$SO$_4$), filtered and concentrated. The residue was purified by flash chromatography on silica gel using a mixture of heptane, ethyl acetate and formic acid (80:20:1) as eluent. Concentration of the appropriate fractions afforded 0.38 g (23% yield) of the desired product as an oil. $^1$H-NMR (300 MHz, CDCl3): δ 0.95-1.00 (m, 6H), 1.30-1.45 (m, 10H), 1.65 (m, 2H), 1.80 (m, 2H), 2.10 (m, 4H), 2.80 (m, 4H), 3.50 (m, 1H), 3.60 (m, 1H), 3.85 (t, 1H), 5.30-5.50 (m, 6H); MS (electro spray): 349.2 [M–H]⁻.

Example 12

Preparation of tert-butyl 2-ethyl-2-((5Z,8Z,11Z,14Z, 17Z)-icosa-5,8,11,14,17-pentaen-1-yloxy)butanoate

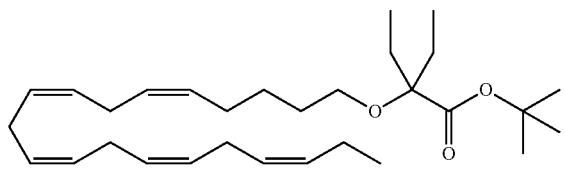 [SMILES: CC/C=C\C/C=C\C/C=C\C/C=C\C/C=C\CCCCOC(CC)(CC)C(=O)OC(C)(C)C]

tert-Butyl 2-((5Z,8Z,11Z,14Z,17Z)-icosa-5,8,11,14,17-pentaen-1-yloxy)butanoate (480 mg, 1.11 mmol) was added dropwise over 30 minutes to a solution of lithium diisopropylamine (LDA) (2.0 M, 750 μL, 1.50 mmol) in dry tetrahydrofuran (10 mL) held at −70° C. under nitrogen. The reaction mixture was stirred for 30 minutes. Ethyl iodide (312 mg, 2.00 mmol) was added in one portion and the resulting mixture was warmed to ambient temperature during 1 hour. The reaction mixture was stirred at ambient temperature for 17 hours. The mixture was poured into saturated NH₄Cl (aq.) (50 mL) and extracted with heptane (2×50 mL). The combined organic phases was washed succesively with brine (50 mL), 0.25 M HCl (50 mL) and brine (50 mL), dried (MgSO₄), filtered and concentrated. The residue was purified by flash chromatography on silica gel using increasingly polar mixtures of heptane and ethyl acetate (100:0→95:5) as eluent. Concentration of the appropriate fractions afforded 343 mg (67% yield) of the title compound as an oil. ¹H NMR (300 MHz, CDCl3): δ 0.84 (t, 6H), 0.99 (td, 3H), 1.35-1.55 (m, 11H), 1.54-1.69 (m, 2H), 1.68-1.87 (m, 4H), 1.99-2.24 (m, 4H), 2.74-2.99 (m, 8H), 3.31 (t, 2H), 5.23-5.52 (m, 10H); MS (electro spray): 401.3 [M–H]⁻

Example 13

Preparation of 2-ethyl-2-((5Z,8Z,11Z,14Z,17Z)-icosa-5,8,11,14,17-pentaen-1-yloxy)butanoic acid

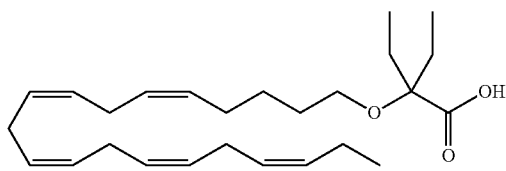 [SMILES: CC/C=C\C/C=C\C/C=C\C/C=C\C/C=C\CCCCOC(CC)(CC)C(=O)O]

A mixture of formic acid (5 ml) and tert-butyl 2-ethyl-2-((5Z,8Z,11Z,14Z,17Z)-icosa-5,8,11,14,17-pentaen-1-yloxy) butanoate (250 mg, 0.55 mmol) was stirred vigorously under nitrogen at room temperature for 4.5 hours. The formic acid was removed in vacuo. The residue was purified by flash chromatography on silica gel using increasingly polar mixtures of heptane and ethyl acetate (100:0→80:20) as eluent. Concentration of the appropriate fractions afforded 163 mg (74% yield) of the title compound as an oil. ¹H NMR (300 MHz, CDCl³): δ 0.86 (t, 6H), 0.99 (t, 3H), 1.36-1.57 (m, 2H), 1.68 (dd, 2H), 1.73-1.98 (m, 4H), 2.11 (tt, 4H), 2.70-3.01 (m, 8H), 3.39 (t, 2H), 5.20-5.56 (m, 10H). MS (electrospray): 481.4 [M+Na]⁺.

Example 14

Preparation of tert-butyl 2-((4Z,7Z,10Z,13Z,16Z, 19Z)-docosa-4,7,10,13,16,19-hexaen-1-yloxy)propanoate

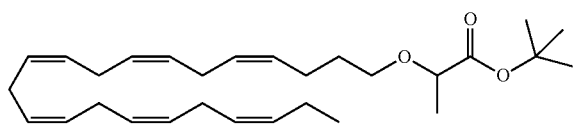 [SMILES: CC/C=C\C/C=C\C/C=C\C/C=C\C/C=C\C/C=C\CCCOC(C)C(=O)OC(C)(C)C]

An aqueous solution of sodium hydroxide (50% (w/w), 6 ml) was added portionwise to a mixture of (5Z,8Z,11Z,14Z, 17Z)-icosa-5,8,11,14,17-pentaen-1-ol (2.01 g, 6.39 mmol), tert-butyl-2-bromobutyrat (2.85 g, 12.8 mmol) and tetrabutylammonium bisulfate (0.65 g, 1.91 mmol) in toluene (12 ml). The reaction mixture was vigorously stirred under N₂-atmosphere and warmed to 50° C. The reaction mixture was stirred at 50° C. for a total of 22 hrs. Additional tert-butyl-2-bromobutyrat (1.43 g, 6.39 mmol) and (1.44 g, 6.44 mmol) was added after 1½ hrs and 3 hrs respectively. The mixture was cooled and added ice-water (~50 ml) and heptane (50 ml), the phases were separated and the organic phase was concentrated under reduced pressure. Flash chromatography on silica gel (30 g) eluting with heptane-heptane/EtOAc (99:1) yielded 2.12 g of the title compound as a liquid. ¹H NMR (300 MHz, CDCl₃) δ 0.94-1.04 (m, 6H), 1.47 (s, 9H), 1.68-1.85 (m, 4H), 1.93-2.20 (m, 4H), 2.80-2.86 (m, 10H), 3.28-3.36 (m, 1H), 3.55-3.63 (m, 2H), 5.27-5.43 (m, 12H)

Example 15

Preparation of 2-((4Z,7Z,10Z,13Z,16Z,19Z)-docosa-4,7,10,13,16,19-hexaen-1-yloxy)butanoic acid

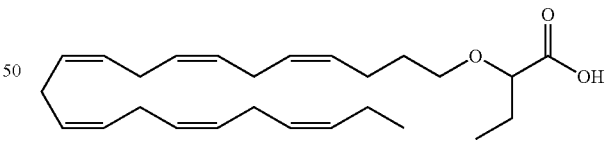

A mixture of tert-butyl 2-((4Z,7Z,10Z,13Z,16Z,19Z)-docosa-4,7,10,13,16,19-hexaen-1-yloxy)propanoate (2.09 g, 4.58 mmol) in HCOOH (9 ml) was stirred at 40° C. under N₂-atmosphere for 6 hrs. The reaction mixture was diluted with diethyl ether (100 mL), washed with water (30 mL), dried (MgSO₄), filtered and evaporated under reduced pressure. Dry-flash on silica gel (50 g) eluting with toluene-toluene (85:15) yielded 1.44 g of the crude title compound. Flash chromatography on silica gel (30 g) eluting with heptane-heptane/(EtOAc w/5% HCCOH) 98:2-95:5-80:20 yielded 1.07 g (58% yield) of the title compound as a liquid. ¹H NMR (200 MHz, CDCl₃) δ 0.97 (t, 3H), 0.99 (t, 3H), 1.64-1.91 (m, 4H), 2.00-2.23 (m, 4H), 2.78-2.87 (m, 10H), 3.42-3.66 (m, 2H), 3.85 (dd, 1H), 5.26-5.46 (m, 12H). MS (electrospray) (neg): 399 (M−H)⁻.

Example 16

Preparation of tert-butyl 2-((3Z,6Z,9Z,12Z,15Z)-octadeca-3,6,9,12,15-pentaen-1-yloxy)butanoate

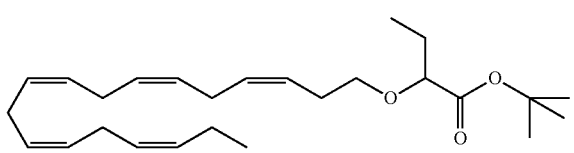 [SMILES: CC/C=C\C/C=C\C/C=C\C/C=C\C/C=C\CCOC(CC)C(=O)OC(C)(C)C]

An aqueous solution of sodium hydroxide (50% (w/w), 6 mL) was added portionwise to a mixture of (3Z,6Z,9Z,12Z,15Z)-octadeca-3,6,9,12,15-pentaen-1-ol (1.66 g, 6.37 mmol), tert-butyl-2-bromobutyrat (2.86 g, 12.8 mmol) and tetrabutylammonium bisulfate (0.65 g, 1.91 mmol) in toluene (12 ml). The reaction mixture was vigorously stirred under $N_2$-atmosphere and warmed to 50° C. The reaction mixture was stirred at 50° C. for a total of 25 hrs. Additional tert-butyl-2-bromobutyrat (1.43 g, 6.41 mmol) and (1.42 g, 6.38 mmol) was added after 1½ hrs and 3 hrs respectively. The mixture was cooled to room temperature and added water (30 mL) and heptane (50 mL), the resulting two phases were separated and the organic phase was dried ($Na_2SO_4$), filtered and evaporated under reduced pressure. Flash chromatography on silica gel (30 g) eluting with heptane-heptane/EtOAc (99:1) yielded 1.55 g of the title compound as a liquid. $^1$H NMR (300 MHz, $CDCl_3$) δ 0.96 (t, 3H), 0.97 (t, 3H), 1.48 (s, 9H), 1.64-1.86 (m, 2H), 2.03-2.12 (m, 2H), 2.39 (dd, J=12.1, 6.7 Hz, 2H), 2.79-2.86 (m, 8H), 3.29-3.37 (m, 1H), 3.57-3.66 (m, 2H), 5.27-5.49 (m, 10H).

Example 17

Preparation of 2-((3Z,6Z,9Z,12Z,15Z)-octadeca-3,6,9,12,15-pentaen-1-yloxy)butanoic acid

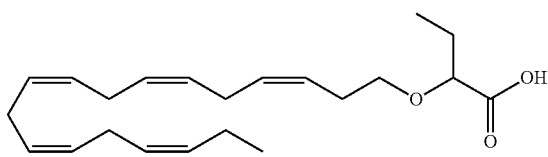 [SMILES: CC/C=C\C/C=C\C/C=C\C/C=C\C/C=C\CCOC(CC)C(=O)O]

A mixture of tert-butyl 2-((3Z,6Z,9Z,12Z,15Z)-octadeca-3,6,9,12,15-pentaen-1-yloxy)butanoate (2.09 g, 4.58 mmol) in HCOOH (9 mL) was stirred at 40° C. under $N_2$-atmosphere for 6 hrs. The reaction mixture was diluted with diethyl ether (100 mL), washed with water (30 mL), dried ($MgSO_4$), filtered and evaporated under reduced pressure. Dry-flash on silica gel (50 g) eluting with toluene-toluene/EtOAc (85:15) yielded 1.44 g of the crude title compound. Flash chromatography on silica gel (30 g) eluting with heptane-heptane/(EtOAc w/5% HCCOH) 98:2-95:5-80:20 yielded 1.07 g (58% yield) of the title compound as a liquid. $^1$H NMR (200 MHz, $CDCl_3$) δ 0.97 (t, 3H), 0.99 (t, 3H), 1.75-1.91 (m, 2H), 2.00-2.15 (m, 2H), 2.35-2.48 (m, 2H), 2.78-2.87 (m, 8H), 3.47-3.62 (m, 2H), 3.86 (dd, 1H), 5.25-5.55 (m, 10H). MS (electrospray) (neg): 345 (M−H)⁻.

Biological Testing

Example 18

Evaluation of PPAR Activation In Vitro

The assays were carried out in vitro using mammalian-one-hybrid assays (M1H) comprising GAL4-DNA binding domain-PPAR-LBD fusion constructs in conjunction with 5×GAL4-sites driven *Photinus pyralis* luciferase reporter constructs in transiently transfected HEK293 cells.

The cells were transfected 4-6 h and grown overnight before compounds were added. Compound incubation was 16-20 h.

*Renilla reniformis* luciferase, driven by a constitutive promoter, was included as internal control to improve experimental accuracy.

The compounds (A-C) and a positive control were tested at six different concentrations in duplicate. The positive controls were GW7647 (PPARα), GW501516 (PPARδ) and rosiglitazone (PPARγ). The efficacy of the controls were set to 100%.

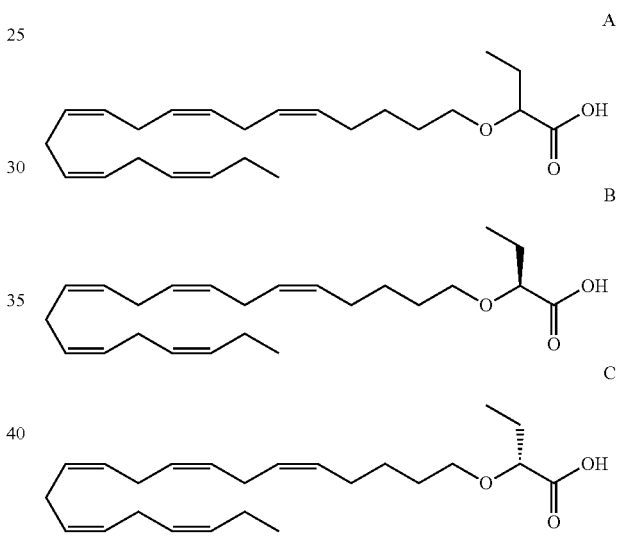

The results are presented in Table 1.

TABLE 1

| | PPAR activation in vitro. | | | | | |
|---|---|---|---|---|---|---|
| | PPARα | | PPARδ | | PPARγ | |
| Compound | $EC_{50}$ | Efficacy | $EC_{50}$ | Efficacy | $EC_{50}$ | Efficacy |
| Pos. ctr. | 0.45 nM | 100% | 0.33 nM | 100% | 22 nM | 100% |
| A | 307 nM | 82% | inactive | inactive | 806 nM | 22% |
| B | 405 nM | 86% | inactive | inactive | 644 nM | 27% |
| C | 167 nM | 54% | inactive | inactive | 515 nM | 25% |

Example 19

Evaluation of the Effects on In Vivo Lipid Metabolism in a Dyslipidemic Mouse Model (APOE*3Leiden Transgenic Mice)

This animal model has proven to be representative of the human situation with respect to plasma lipoprotein levels and its responsiveness to hypolipidemic drugs, such as statins and fibrates, and nutritional intervention. In addition, depending on the level of plasma cholesterol, APOE*3Leiden mice develop atherosclerotic lesions in the aorta resembling those found in humans with respect to cellular composition and morphological and immunohistochemical characteristics.

Female APOE*3Leiden mice were put on a semi-synthetic Western-type diet (WTD, 15% cocoa butter, 40% sucrose and 0.25% cholesterol; all w/w). With this diet the plasma cholesterol level reached mildly elevated levels of approximately 12-15 mmol/l. After a 4 week run-in period the mice were sub-divided into groups of 10 mice each, matched for plasma cholesterol, triglycerides and body weight (t=0).

The test substances were administered orally as admix to the Western-type diet. To facilitate the mixing of the compounds sunflower oil was added to a total oil volume of 10 mL/kg diet.

At t=0 and 4 weeks blood samples were taken after a 4 hour-fast to measure plasma cholesterol and triglycerides.

The test substance (A) was tested at 0.3 mmol/kg bw/day. The reference (Omega-3 acid ethyl esters, Omacor™, Lovaza™) was tested at 3.3 mmol/kg bw/day.

The results are shown in FIG. 1.

Example 20

Evaluation of the Effects on In Vivo Lipid Metabolism in a Dyslipidemic Mouse Model (APOE*3Leiden.CETP Transgenic Mice)

The APOE*3Leiden.CETP transgenic mouse is a model where the human cholesterol ester transfer protein has been introduced to the APOE*3Leiden transgenic mouse. This results in a more human-like lipoprotein profile. This model is very well suited for testing the effects of drugs on plasma HDL and triglyceride levels.

Female APOE*3Leiden.CETP mice were put on a semi-synthetic modified Western-type diet (0.15% cholesterol and 15% saturated fat, all w/w). With this diet the plasma cholesterol level reaches moderately elevated levels of about 13-15 mmol/l and triglyceride levels of approximately 3 mmol/l. After a 4 week run-in period the mice were sub-divided into groups of 6 mice each, matched primarily for plasma cholesterol, triglycerides and body weight and secondarily for HDL-cholesterol (t=0).

The test substances were administered orally as admix to the Western-type diet.

At t=0 and 4 weeks blood samples were taken after a 4 hour-fast to measure plasma cholesterol, HDL-cholesterol and triglycerides.

The test substance (A) was tested at 0.18 mmol/kg bw/day. The reference (Fenofibrate) was tested at 10 mg/kg bw/day.

Figure 2:
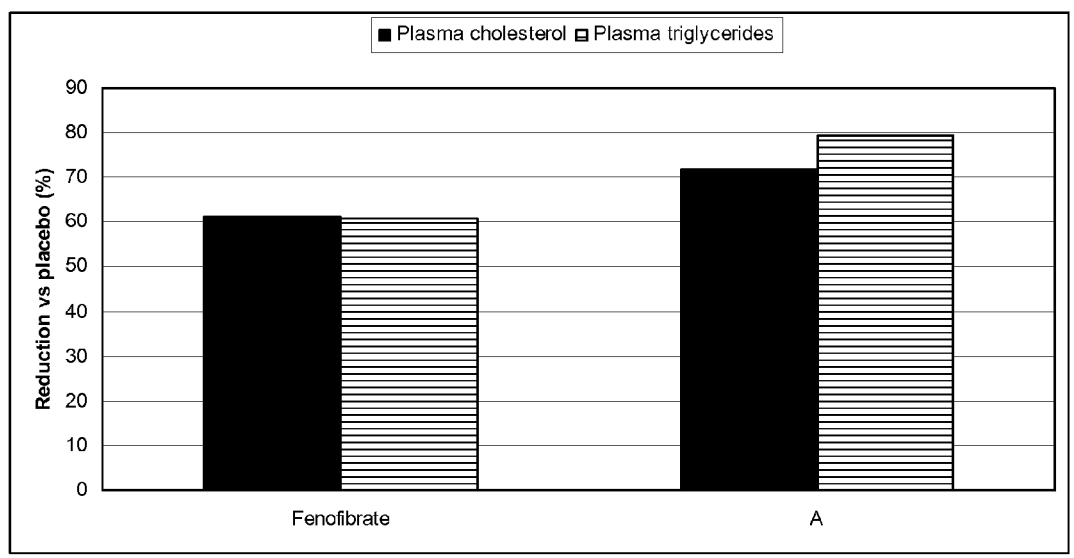
FIG. 2: Cholesterol and triglyceride levels in APOE*3Leiden.CETP mice after administration of one embodiment of the present disclosure and fenofibrate.
Figure 3:
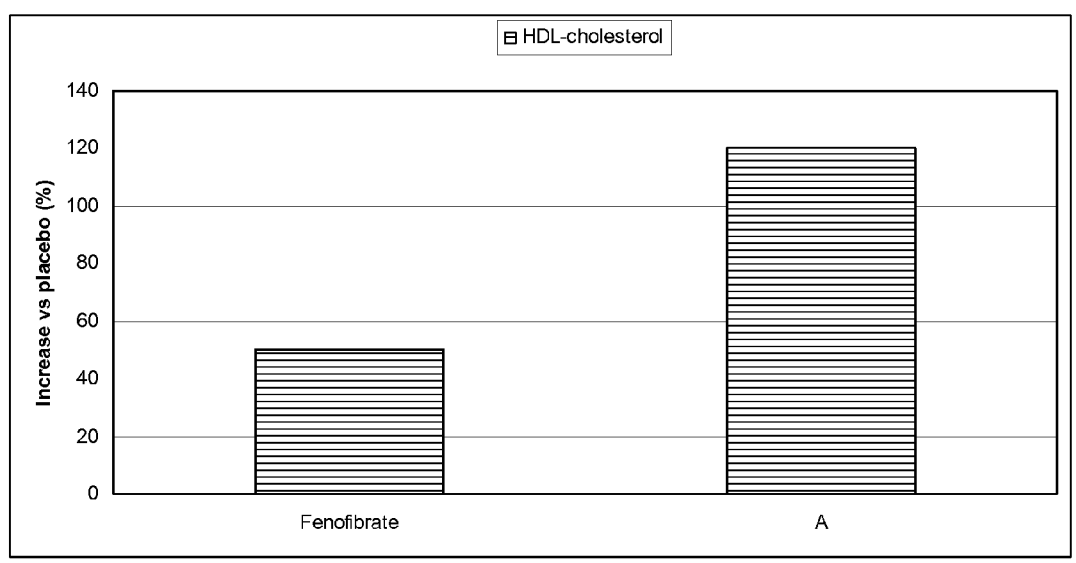
FIG. 3: HDL levels in APOE*3Leiden.CETP mice after administration of one embodiment of the present disclosure and fenofibrate.

The results are shown in FIGS. 2 and 3.

Example 21

Evaluation of the Effects on In Vivo Atherosclerosis Development in a Mouse Model (APOE*3Leiden.CETP Transgenic Mice)

This animal model has proven to be representative of the human situation with respect to plasma lipoprotein levels and its responsiveness to hypolipidemic drugs (like statins, fibrates etc.) and nutritional intervention. APOE*3Leiden.CETP mice develop atherosclerotic lesions in the aorta resembling those found in humans with respect to cellular composition and morphological and immunohistochemical characteristics.

Female APOE*3Leiden.CETP mice were put on a Western-type diet (WTD) with 0.15% cholesterol and 15% saturated fat; resulting in plasma cholesterol levels of about 13-15 mM. After a 3 week run-in period on the WTD, the mice were sub-divided into 4 groups of 15 mice, control (no treatment), compound A, fenofibrate and a low-cholesterol diet. The groups were matched for body weight, plasma total cholesterol (TC), HDL cholesterol (HDL-C) and triglycerides (TG) after 4 h fasting (t=0).

The test substances were administered orally as admix to the Western-type diet. To facilitate the mixing of the compounds sunflower oil was added to a total oil volume of 10 mL/kg diet. The test compound (A) was tested at initially at 0.1 mmol/kg bw/day and reduced to 0.04 mmol/kg bw/day at 4 weeks. The initial dose was based on a prior dose-finding study to establish the required dosage that would reduce VLDL/LDL cholesterol by 25-30%.

The dosage of fenofibrate was initially 10 mg/kg bw/day and was reduced to 4.2 mg/kg bw/day (to parallel reductions in VLDL/LDL induced by compound A).

At t=0, 4, 8, 12 and 14 weeks blood samples were taken after a 4 hour-fast to measure food intake, total plasma cholesterol, HDL cholesterol and triglycerides and lipoprotein profiles. Atherosclerosis development in the aortic root (lesion number, total lesion area and lesion severity) was assessed at study-end.

The invention shall not be limited to the shown embodiments and examples.

The invention claimed is:

1. A lipid compound of formula:

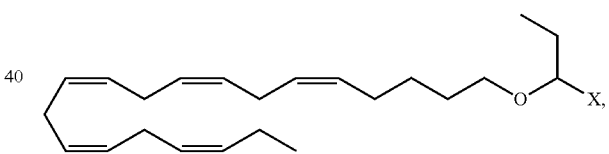

wherein

X is a carboxylic acid or a derivative thereof, or a pharmaceutically acceptable salt thereof.

2. The lipid compound according to claim 1, wherein the compound is present as its R enantiomer.

3. The lipid compound according to claim 1, wherein the compound is present as its S enantiomer.

4. The lipid compound according to claim 1, wherein the salt is chosen from

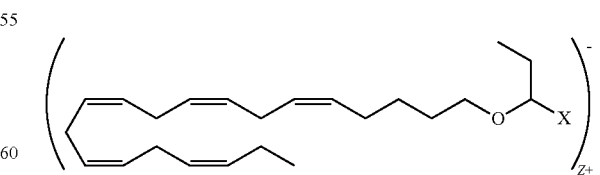

wherein X is COO$^-$, and Z$^+$ is chosen from Li$^+$, Na$^+$, K$^+$, NH$_4^+$, a protonated primary amine, a protonated aminopyridine, a protonated secondary amine, a protonated tertiary amine, a protonated guanidine, or a protonated heterocycle;

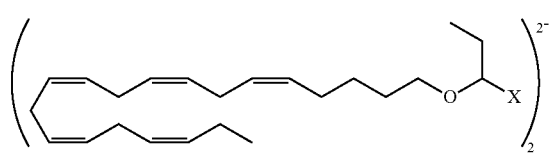

wherein X is COO⁻, and $Z^{2+}$ is chosen from $Mg^{2+}$, $Ca^{2+}$, or a diprotonated diamine; or

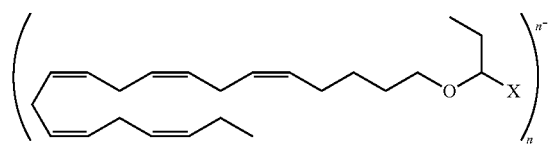

wherein X is COO⁻ and $Z^{n+}$ is protonated Chitosan:

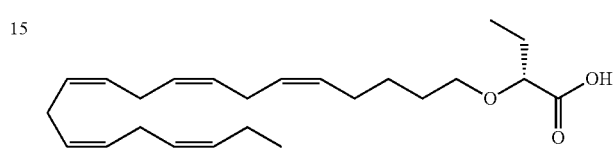

wherein n and m are integers.

5. The lipid compound according to claim 1, wherein X is a carboxylic acid or a derivative thereof in the form of an ester, a mono-glyceride, a 2-mono-glyceride, a diglyceride, a triglyceride, or a phospholipid.

6. The lipid compound according to claim 5, wherein X is a carboxylic acid derivative in the form of an ethyl ester.

7. The lipid compound according to claim 5, wherein X is a carboxylic acid derivative in the form of a 2-mono-glyceride.

8. The lipid compound according to claim 5, wherein X is a carboxylic acid.

9. The lipid compound according to claim 1, in a mixture of enantiomers or in racemic form.

10. The lipid compound according to claim 5, wherein the compound is present as its R enantiomer at the carbon attached to the oxygen, the ethyl group, and X.

11. The lipid compound according to claim 5, wherein the compound is present as its S enantiomer at the carbon attached to the oxygen, the ethyl group, and X.

12. The A lipid compound according to claim 1, wherein the compound is:

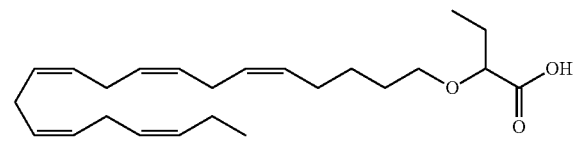 [SMILES: CC/C=C\C/C=C\C/C=C\C/C=C\C/C=C\CCCCOC(CC)C(=O)O]

2-((5Z,8Z,11Z,14Z,17Z)-icosa-5,8,11,14,17-pentaenyloxy)butanoic acid;

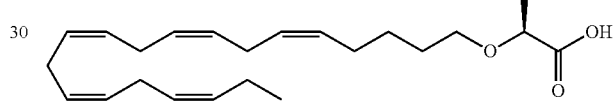

(R)-2-((5Z,8Z,11Z,14Z,17Z)-icosa-5,8,11,14,17-pentaenyloxy)butanoic acid;

(S)-2-((5Z,8Z,11Z,14Z,17Z)-icosa-5,8,11,14,17-pentaenyloxy)butanoic acid;

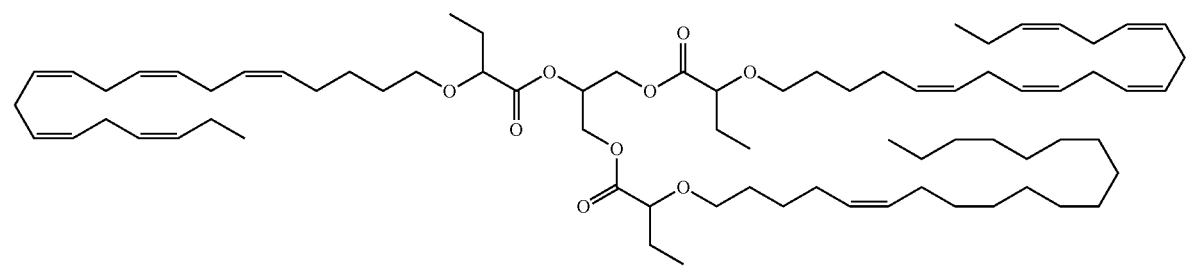 [SMILES: CC/C=C\C/C=C\C/C=C\C/C=C\C/C=C\CCCCOC(CC)C(=O)OCC(COC(=O)C(CC)OCCCC/C=C\CCCCCCCCCCCCCC)OC(=O)C(CC)OCCCC/C=C\C/C=C\C/C=C\C/C=C\C/C=C\CC]

propane-1,2,3-triyltris(2-((5Z,8Z,11Z,14Z,17Z)-icosa-5,8,11,14,17-pentaen-1-yloxy)butanoate;

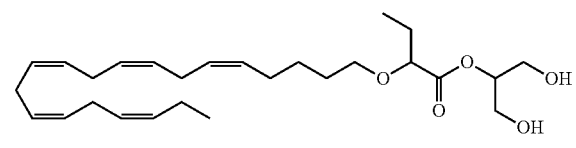 [SMILES: CC/C=C\C/C=C\C/C=C\C/C=C\C/C=C\CCCCOC(CC)C(=O)OC(CO)CO]

47
1,3-dihydroxypropan-2-yl 2-((5Z,8Z,11Z,14Z,17Z)-icosa-5,8,11,14,17-pentaen-1-yloxy)butanoate;
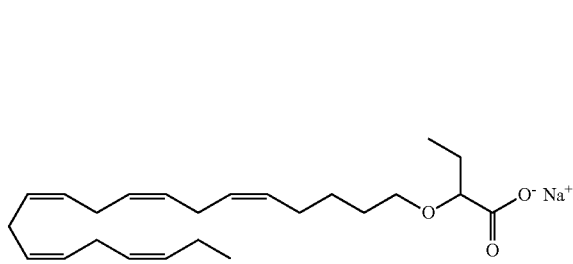 [SMILES: CC/C=C\C/C=C\C/C=C\C/C=C\C/C=C\CCCCOC(CC)C(=O)[O-] ; [Na+]]
sodium 2-((5Z,8Z,11Z,14Z,17Z)-icosa-5,8,11,14,17-pentaen-1-yloxy)butanoate;
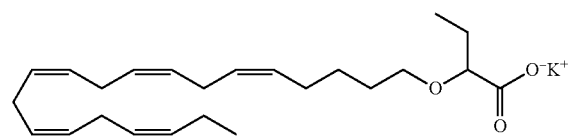
48
potassium 2-((5Z,8Z,11Z,14Z,17Z)-icosa-5,8,11,14,17-pentaen-1-yloxy)butanoate;
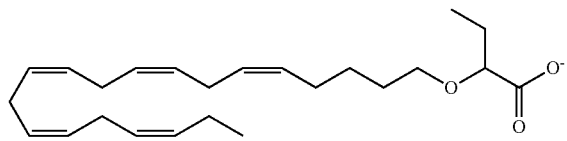
tert-butyl-ammonium 2-((5Z,8Z,11Z,14Z,17Z)-icosa-5,8,11,14,17-pentaen-1-yloxy)butanoate;
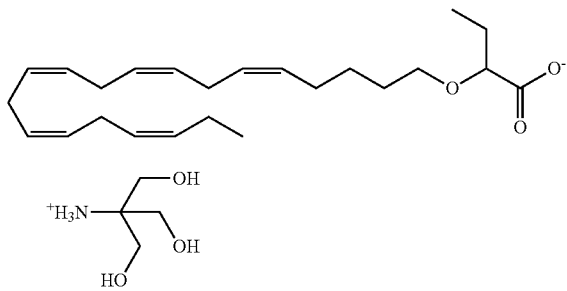 [SMILES: CC/C=C\C/C=C\C/C=C\C/C=C\C/C=C\CCCCOC(CC)C(=O)[O-] ; [NH3+]C(CO)(CO)CO]
1,3-dihydroxy-2-(hydroxymethyl)propan-2-ammonium 2-((5Z,8Z,11Z,14Z,17Z)-icosa-5,8,11,14,17-pentaen-1-yloxy)butanoate;
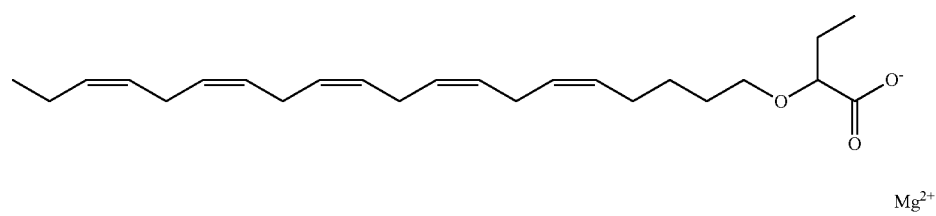
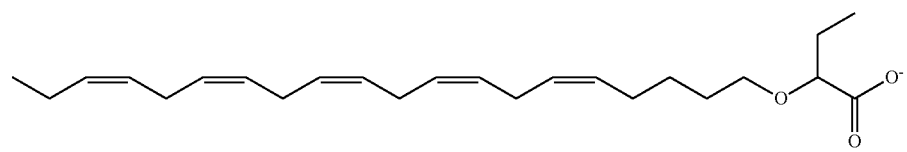
magnesium 2-((5Z,8Z,11Z,14Z,17Z)-icosa-5,8,11,14,17-pentaen-1-yloxy)butanoate; or

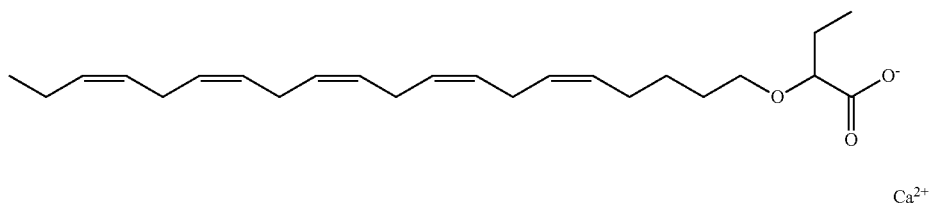

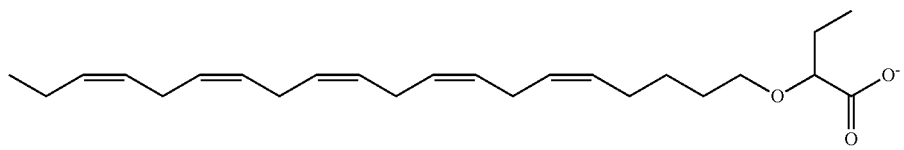

calcium 2-((5Z,8Z,11Z,14Z,17Z)-icosa-5,8,11,14,17-pentaen-1-yloxy)butanoate.

13. A pharmaceutical composition comprising:

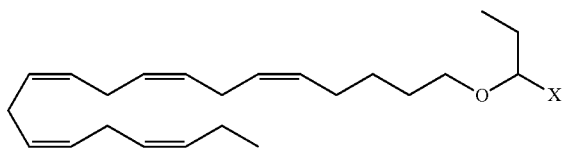

wherein

X is a carboxylic acid or a derivative thereof, or a pharmaceutically acceptable salt thereof and a pharmaceutically acceptable carrier, excipient or diluent, or any combination thereof.

14. The pharmaceutical composition according to claim 13, further comprising a pharmaceutically acceptable antioxidant.

15. The pharmaceutical composition according to claim 13, formulated for oral administration.

16. The pharmaceutical composition according to claim 13, wherein the at least one lipid compound is administered in a daily dose ranging from 1 mg to 3 g.

17. The pharmaceutical composition according to claim 16, wherein the daily dose ranges from 50 mg to 1 g.

18. The pharmaceutical composition according to claim 16, wherein the daily dose ranges from 50 mg to 500 mg.

19. The pharmaceutical composition according to claim 16, wherein the daily dose ranges from 10 mg to 2 g.

20. The pharmaceutical composition according to claim 16, wherein the daily dose ranges from 100 mg to 1 g.

21. The pharmaceutical composition according to claim 16, wherein the daily dose ranges from 100 mg to 500 mg.

22. The pharmaceutical composition according to claim 16, wherein the daily dose ranges from 100 mg to 250 mg.

23. The pharmaceutical composition according to claim 13, in the form of a gelatin capsule, a tablet, or a sachet.

24. The pharmaceutical composition according to claim 13, for use as a medicament.

25. A method of treating atherosclerosis comprising administering to a subject in need thereof at least one compound according to claim 1.

26. A method of treating dyslipidemia or mixed dyslipidemia comprising administering to a subject in need thereof at least one compound according to claim 1.

27. The method according to claim 26, wherein the dyslipidemia is hypertriglyceridemia.

28. A method of lowering cholesterol comprising administering to a subject in need thereof at least one compound according to claim 1.

29. The method according to claim 28, wherein the cholesterol is non-HDL cholesterol.

30. The method according to claim 28, wherein the cholesterol is LDL and/or VLDL cholesterol.

31. A method of raising HDL cholesterol comprising administering to a subject in need thereof at least one compound according to claim 1.

32. A method for the production of 2-((5Z,8Z,11Z,14Z,17Z)-icosa-5,8,11,14,17-pentaenyloxy)butanoic acid comprising a) reacting (5Z,8Z,11Z,14Z,17Z)-icosa-5,8,11,14,17-pentaen-1-ol with t-butyl 2-bromobutyrate;

b) converting the ester that results from step a) into a carboxylic acid; and c) isolating said 2-((5Z,8Z,11Z,14Z,17Z)-icosa-5,8,11,14,17-pentaenyloxy)butanoic acid.

33. The pharmaceutical composition according to claim 14, wherein the antioxidant is tocopherol or 3-tert-butyl-4-hydroxyanisole.

34. A pharmaceutical formulation comprising:

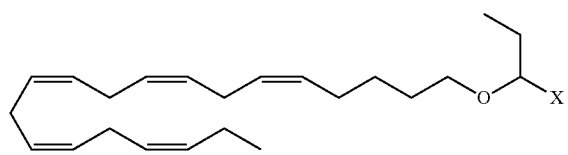

wherein

X is a carboxylic acid or a derivative thereof, or a pharmaceutically acceptable salt thereof;

an emulsifier, a viscosity modifier, an antioxidant, and a fatty substance.

35. The pharmaceutical formulation according to claim 34, wherein the antioxidant is 3-tert-butyl-4-hydroxyanisole.

36. The pharmaceutical formulation according to claim 34, wherein the formulation is in the form of an emulsion.

37. The pharmaceutical formulation according to claim 34, further comprising gelatin.

38. A pharmaceutical formulation comprising a lipid chosen from

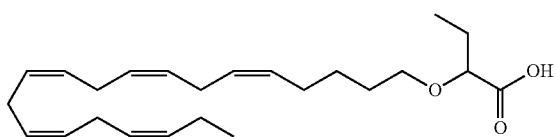 [SMILES: CC/C=C\C/C=C\C/C=C\C/C=C\C/C=C\CCCCOC(CC)C(=O)O]

2-((5Z,8Z,11Z,14Z,17Z)-icosa-5,8,11,14,17-pentaenyloxy)butanoic acid;

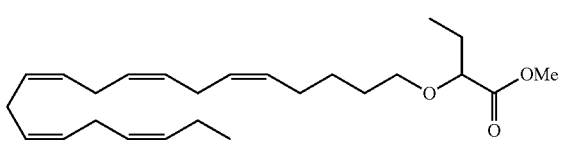 [SMILES: CC/C=C\C/C=C\C/C=C\C/C=C\C/C=C\CCCCOC(CC)C(=O)OC]

methyl (2-((5Z,8Z,11Z,14Z,17Z)-icosa-5,8,11,14,17-pentaen-1-yloxy)butanoate;

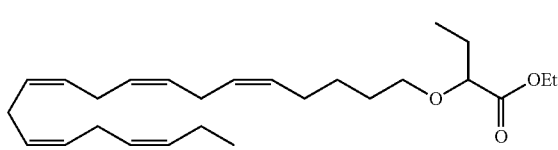 [SMILES: CC/C=C\C/C=C\C/C=C\C/C=C\C/C=C\CCCCOC(CC)C(=O)OCC]

ethyl 2-((5Z,8Z,11Z,14Z,17Z)-icosa-5,8,11,14,17-pentaen-1-yloxy)butanoate;
an emulsifier,
a viscosity modifier,
an antioxidant,
and a fatty substance.

39. The pharmaceutical formulation according to claim 38, wherein the antioxidant is 3-tert-butyl-4-hydroxyanisole.

40. The pharmaceutical formulation according to claim 38, wherein the formulation is in the form of an emulsion.

41. The pharmaceutical formulation according to claim 38, further comprising gelatin.

42. The lipid compound according to claim 1, wherein the carboxylic acid derivative is a carboxamide.

43. The lipid compound according to claim 42, wherein the carboxamide is chosen from N-methyl carboxamide, N,N-dimethyl carboxamide, N-ethyl carboxamide, and N,N-diethyl carboxamide.

44. The lipid compound according to claim 1 that is

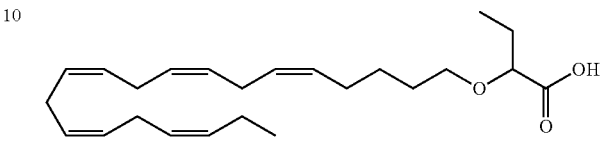

2-((5Z,8Z,11Z,14Z,17Z)-icosa-5,8,11,14,17-pentaenyloxy)butanoic acid.

45. The lipid compound according to claim 1 that is

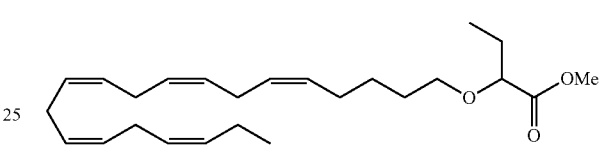

methyl 2-((5Z,8Z,11Z,14Z,17Z)-icosa-5,8,11,14,17-pentaen-1-yloxy)butanoate.

46. The lipid compound according to claim 1 that is

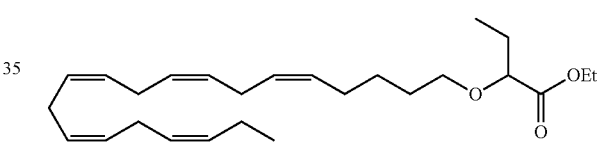

ethyl 2-((5Z,8Z,11Z,14Z,17Z)-icosa-5,8,11,14,17-pentaen-1-yloxy)butanoate.

* * * * *

UNITED STATES PATENT AND TRADEMARK OFFICE
CERTIFICATE OF CORRECTION

PATENT NO. : 8,735,436 B2  
APPLICATION NO. : 13/319101  
DATED : May 27, 2014  
INVENTOR(S) : Ragnar Hovland et al.

Page 1 of 1

It is certified that error appears in the above-identified patent and that said Letters Patent is hereby corrected as shown below:

In the Claims

Claim 12, column 46, between lines 35 and 50,

"
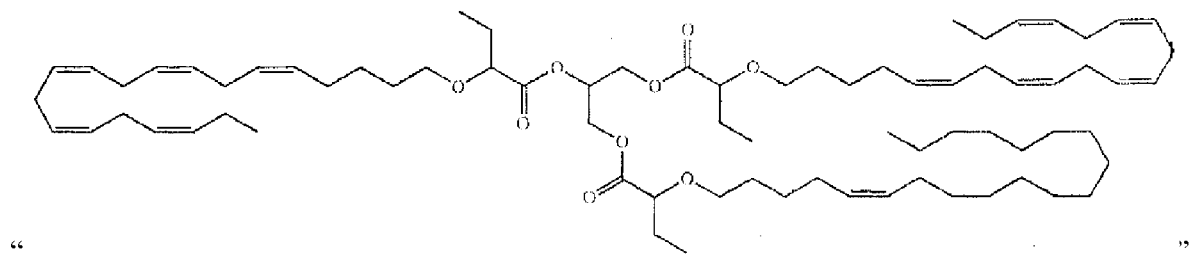
"

should read

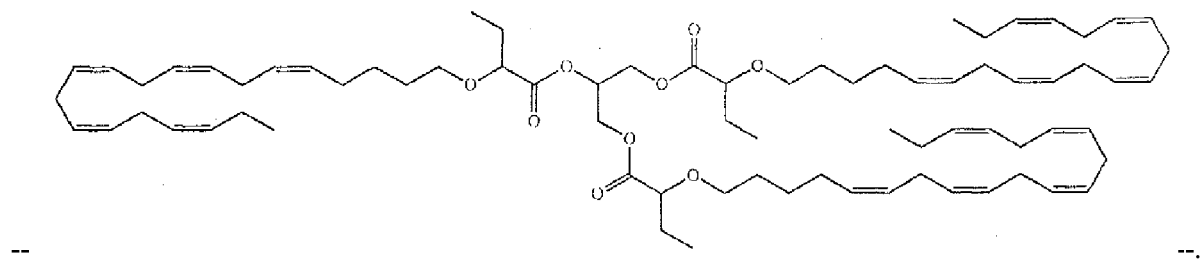

--                                                                                  --.

Claim 12, column 46, line 50, "triyltris" should read --triyl tris--.

Signed and Sealed this  
Eleventh Day of November, 2014

Michelle K. Lee  
*Deputy Director of the United States Patent and Trademark Office*